(12) United States Patent
Kain et al.

(10) Patent No.: US 11,827,932 B2
(45) Date of Patent: Nov. 28, 2023

(54) METHODS AND COMPOSITIONS FOR NUCLEIC ACID SEQUENCING

(71) Applicant: Illumina, Inc., San Diego, CA (US)

(72) Inventors: Robert C. Kain, San Diego, CA (US); Xiaohai Liu, Cambridge (GB); Wenyi Feng, San Diego, CA (US); Bernard Hirschbein, San Francisco, CA (US); Helmy A. Eltoukhy, Atherton, CA (US); Xiaolin Wu, Cambridge (GB); Geoffrey Paul Smith, Cambridge (GB); Jonathan Mark Boutell, Cambridge (GB); Thomas Joseph, San Diego, CA (US); Randall Smith, San Diego, CA (US); Min-Jui Richard Shen, Poway, CA (US); Carolyn Tregidgo, Hertfordshire (GB); Kay Klausing, San Diego, CA (US)

(73) Assignee: Illumina, Inc., San Diego, CA (US)

(*) Notice: Subject to any disclaimer, the term of this patent is extended or adjusted under 35 U.S.C. 154(b) by 200 days.

(21) Appl. No.: 17/153,309

(22) Filed: Jan. 20, 2021

(65) Prior Publication Data

US 2021/0139978 A1    May 13, 2021

Related U.S. Application Data

(63) Continuation of application No. 16/405,679, filed on May 7, 2019, now Pat. No. 10,900,077, which is a
(Continued)

(51) Int. Cl.
*C12Q 1/68* (2018.01)
*C12Q 1/6874* (2018.01)
*C12Q 1/6869* (2018.01)

(52) U.S. Cl.
CPC ......... *C12Q 1/6874* (2013.01); *C12Q 1/6869* (2013.01)

(58) Field of Classification Search
CPC ...................................................... C12Q 1/68
(Continued)

(56) References Cited

U.S. PATENT DOCUMENTS 6,723,513 B2    4/2004  Lexow
6,833,246 B2    12/2004 Balasubramanian
(Continued)

FOREIGN PATENT DOCUMENTS

CN            200976        10/2009
CN            101565746     10/2009
(Continued)

OTHER PUBLICATIONS

Illumina, Inc., 2018, iSeq™ 100 Sequencing System, Pub. No. 770-20170-020-B QB 5473, 4 pp.
(Continued)

*Primary Examiner* — Aaron A Priest
(74) *Attorney, Agent, or Firm* — Knobbe, Martens, Olson & Bear, LLP

(57) ABSTRACT

The present disclosure provides methods and systems for detecting multiple different nucleotides in a sample. In particular, the disclosure provides for detection of multiple different nucleotides in a sample utilizing fewer detection moieties than the number of nucleotides being detected and/or fewer imaging events than the number of nucleotides being detected.

16 Claims, 13 Drawing Sheets

Related U.S. Application Data continuation of application No. 15/207,892, filed on Jul. 12, 2016, now Pat. No. 10,287,629, which is a continuation of application No. 13/624,200, filed on Sep. 21, 2012, now Pat. No. 9,453,258.

(60) Provisional application No. 61/619,878, filed on Apr. 3, 2012, provisional application No. 61/538,294, filed on Sep. 23, 2011.

(58) Field of Classification Search
USPC .......................................................... 435/6.1
See application file for complete search history.

(56) References Cited

U.S. PATENT DOCUMENTS

| | | | |
|---|---|---|---|
| 6,911,345 | B2 | 6/2005 | Quake et al. |
| 7,033,754 | B2 | 4/2006 | Chee |
| 7,060,431 | B2 | 6/2006 | Chee et al. |
| 7,226,734 | B2 | 6/2007 | Chee et al. |
| 7,455,971 | B2 | 11/2008 | Chee et al. |
| 7,592,435 | B2 * | 9/2009 | Milton ............... C12Q 1/686 435/6.12 |
| 7,771,973 | B2 | 8/2010 | Milton et al. |
| 7,816,503 | B2 | 10/2010 | Milton et al. |
| 9,222,132 | B2 | 12/2015 | Drmanac |
| 9,453,258 | B2 | 9/2016 | Kain et al. |
| 2002/0164629 | A1 | 11/2002 | Quake et al. |
| 2004/0014096 | A1 | 1/2004 | Anderson et al. |
| 2005/0181394 | A1 | 8/2005 | Steemers et al. |
| 2006/0160081 | A1 * | 7/2006 | Milton ............... C12Q 1/6869 435/6.12 |
| 2007/0219367 | A1 | 9/2007 | Shchepinov et al. |
| 2009/0325172 | A1 | 12/2009 | Milton et al. |
| 2010/0009353 | A1 | 1/2010 | Barnes et al. |
| 2010/0092960 | A1 | 4/2010 | Fehr |
| 2010/0304368 | A1 | 12/2010 | Cherkasov et al. |
| 2010/0317531 | A1 | 12/2010 | Balasubramanian et al. |
| 2011/0039259 | A1 * | 2/2011 | Ju ............... C12Q 1/6876 435/6.12 |
| 2012/0052489 | A1 * | 3/2012 | Gordon ............... C12Q 1/6869 435/6.1 |
| 2014/0378321 | A1 | 12/2014 | Drmnac |
| 2015/0111763 | A1 | 4/2015 | Eshoo |

FOREIGN PATENT DOCUMENTS

| | | | |
|---|---|---|---|
| CN | 101570784 | | 11/2009 |
| CN | 200910026892 | | 11/2009 |
| WO | WO 2004018493 | | 3/2004 |
| WO | WO-2004018493 A1 * | | 3/2004 ............ C07H 19/04 |
| WO | WO 2004018497 | | 3/2004 |
| WO | WO 2005102176 | | 11/2005 |
| WO | WO 2006074351 | | 7/2006 |
| WO | WO 2006111729 | | 10/2006 |
| WO | WO 07/020457 A2 | | 2/2007 |
| WO | WO 07/020457 A3 | | 10/2007 |
| WO | WO-2007135368 A2 * | | 11/2007 ......... A61K 49/0041 |
| WO | WO 08/005673 A2 | | 1/2008 |
| WO | WO 08/042067 A2 | | 4/2008 |
| WO | WO 2008092150 | | 7/2008 |
| WO | WO 2008092155 | | 7/2008 |
| WO | WO 08/042067 A3 | | 10/2008 |
| WO | WO 08/005673 A3 | | 11/2008 |
| WO | WO 09/051807 A1 | | 4/2009 |
| WO | WO-2009051807 A1 * | | 4/2009 ............ C07H 19/06 |
| WO | WO 2009054922 | | 4/2009 |
| WO | WO 09/097368 A2 | | 8/2009 |
| WO | WO 2009097368 | | 8/2009 |
| WO | WO 09/097368 A3 | | 10/2009 |
| WO | WO 2010117804 | | 10/2010 |

OTHER PUBLICATIONS

"Table of Fluorochromes", 1-6.
"Translation of Patent 200910026892.1 from Chinese into English", Application No. 20091 0026892.1, Application Publication Date Apr. 11, 2009.
Bates et al., "Multicolor Super-Resolution Imaging with Photo-Switchable Fluorescent Probes", Science 317, 2007, 1749-1753.
Bentley et al., "Accurate whole human genome sequencing using reversible terminator chemistry", Nature, vol. 456, 2008, 53-59.
Database WPI, "AN 2009-093300; XP002689368", Thomson Scientific, London, GB, CN 101565746 (Univ Southeast) (Oct. 28, 2009) *abstract*, Week 200976, 3 pages.
Database WPI, "AN 2009-R25953; XP-002689367", Thomson Scientific London, GB CN 101570784 (Univ Southeast) (Nov. 4, 2009) *abstract*, Week 200979, Week 200979, 3 pages.
Dempsey et al., "Photoswitching Mechanism of Cyanine Dyes", J Am Chem Soc 131, Dec. 4, 2009, 18192-18193.
EP12766838.2, "Brief Communication mailed", dated Apr. 17, 2018, 36 pages.
EP17180583, "European Search Report", dated Dec. 5, 2017, 4 pages.
Guillier et al., "Linkers and cleavage Strategies in Solid-Phase Organic Synthesis and Combinatorial Chemistry", Chem. Rev. 100, 2000, 2091-2157.
Ju et al., "Four-Color DNA Sequencing by Synthesis Using Cleavable Florescent Nucleotide Reversible Terminators", PNAS vol. 103, No. 52, 2006, 19635-19640.
Karow, "AGBT: Illumina, Broad Institute Show Performance Data for NextSeq 500, HiSeq X Ten", GenomeWeb, Feb. 18, 2014, pp. 1-4.
Kircher et al., "Improved base calling for the Illumina Fenome Analyzer using machine learning strategies", Genome Biology 2009, vol. 10, No. 8, Aug. 14, 2009, R83.
Kricka et al., "Analytical Ancestry: "Firsts" in Fluorescent Labeling of Nucleosides, Nucleotides, and Nucleic Acids", Clinical Chemistry 55:4, 2009, 670-683.
Li et al., "A photocleavable fluorescent nucleotide for DNA sequencing and analysis,", Proc. Natl. Acad. Sci. 100:414-419 (2003), 2003, 414-419.
Meldrum, "Automation for Genomics, Part One: Preparation for Sequencing", Genome Res. 1 O; Downloaded from genome.cshlp.org on Mar. 21, 2011, 2000, 1081-1092.
Metzker, "Applications of Next-Generation Sequencing: Sequencing technologies-the next generation", Nature Reviews Genetics, Nature Publishing Group, GB, vol. 11 (1 ), Jan. 1, 2010, 31-46.
Pourmand et al., "Direct electrical detection of DNA synthesis", Proc. Natl. Acad. Sci. vol. 103, No. 17, Apr. 25, 2006, 6466-6470.
Thomson Scientific, Database WPI, Week 200976, AN 2009-093300, XP002689368, & CN 101 565 746 Abstract, Oct. 28, 2009, 3 pages.
Thomson Scientific, Database WPI, Week 200979, XP002689367, & CN 101 570 784, Abstract, Nov. 4, 2009, 3 pages.
Guo, J, et al., "Four-color DNA sequencing with 3'-O-modified nucleotide reversible terminators and chemically cleavable fluorescent dideooxynucleotides", PNAS, 105(27), Jul. 8, 2008, 9145-9150.
Wikipedia, "Pyrosequencing", Downloaded on Mar. 7, 2019, Mar. 7, 2019, 3 pages.

* cited by examiner

Image 1

| | Image 1 |
|---|---|
| A | 0.50 |
| C | 0.75 |
| G | 0.25 |
| T | 1.0 |

METHODS AND COMPOSITIONS FOR NUCLEIC ACID SEQUENCING

The present application is a continuation of U.S. patent application Ser. No. 16/405,679, filed on May 7, 2019, to be issued as U.S. Pat. No. 10,900,077, which is a continuation of U.S. patent application Ser. No. 15/207,892, filed on Jul. 12, 2016, now U.S. Pat. No. 10,287,629, which is a continuation of U.S. patent application Ser. No. 13/624,200, filed Sep. 21, 2012, now U.S. Pat. No. 9,453,258, which claims priority to U.S. Application Ser. No. 61/619,878 filed Apr. 3, 2012 and U.S. Application Ser. No. 61/538,294 filed Sep. 23, 2011, the disclosures of all of which are incorporated herein by reference in their entireties.

BACKGROUND

The detection of analytes such as nucleic acid sequences that are present in a biological sample has been used as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting analytes such as nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of thousands of nucleic acids all in a single sequencing run. The instrumentation that performs such methods is typically large and expensive since the current methods typically rely on large amounts of expensive reagents and multiple sets of optic filters to record nucleic acid incorporation into sequencing reactions.

It has become clear that the need for high-throughput, smaller, less expensive DNA sequencing technologies will be beneficial for reaping the rewards of genome sequencing. Personalized healthcare is moving toward the forefront and will benefit from such technologies; the sequencing of an individual's genome to identify potential mutations and abnormalities will be crucial in identifying if a person has a particular disease, followed by subsequent therapies tailored to that individual. To accommodate such an aggressive endeavour, sequencing should move forward and become amenable to high throughput technologies not only for its high throughput capabilities, but also in terms of ease of use, time and cost efficiencies, and clinician access to instruments and reagents.

SUMMARY

Existing fluorescence based sequencing reactions distinguish between the incorporation of different nucleotides into a growing nucleic acid strand by attaching a fluorescent moiety to each of four nucleotides, A T C and G. Typically, each of the fluorescent moieties excites and emits at different wavelengths and thus the target sequence is determined. Conversely, the present disclosure provides for determination of a sequence, for example a nucleic acid sequence, using a minimal dye set, minimal excitation light sources, and minimal optical emission filters while still allowing for differentiation of the incorporation of all four nucleotides in a sequencing reaction. The present disclosure provides methods and compositions amenable to any fluorescent system where more than one analyte for detection is desired. However, particular advantages are found when applying the methods herein to sequencing methodologies such as sequence by synthesis methodologies.

Instruments and systems for detecting four color fluorescence sequencing are large and expensive to run, not only cost of the instrument but the reagents as well and are thus not very attractive to smaller and more capital constrained locations. Methods and compositions that would decrease the costs and/or size associated with four color fluorescence detection, for example for sequencing genomes, would provide investigators more efficient tools in terms of time efficiency, lower reagent usage, smaller less expensive instrumentation, and the like for use in their research endeavours.

Embodiments of the present disclosure provide those options by providing investigators with methods and compositions for determination of a polymer sequence, for example a nucleic acid sequence, comprising using a minimal dye set, minimal light sources, and minimal excitation/emission filters while still allowing for differentiation of monomer types (e.g., different nucleotides) incorporated in a sequencing reaction.

Embodiments described herein provide for determining the sequence of a nucleic acid based on event timing and memorializing those events in "time space". The present disclosure provides embodiments for the use of one dye, or a plurality of dyes of the same or similar excitation/emission spectra, or two or more dyes of different fluorescence spectra, to determine the presence of analytes, for example nucleotides, in a sample, using time space based imaging events. As described herein, time space sequencing reactions utilize one or more chemistries and imaging events or steps to differentiate between a plurality of analytes, for example four nucleotides, that are incorporated into a growing nucleic acid strand during a sequencing reaction.

In some embodiments, fewer than four different colours can be detected in a mixture having four different nucleotides while still resulting in the determination of the four different nucleotides, for example in a sequencing reaction. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels.

The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

In this example, an array of nucleic acid features can be treated with all four nucleotide types such that an extension event occurs at substantially all of the features prior to a detection event and the features are detected in as few as one image event, in as few as two image events during the detection event. A first image obtained using the first excitation wavelength and emission in the first channel can detect and show features that incorporate the first and/or third nucleotide type (e.g. A and/or T). A second image obtained using the second excitation wavelength and emission in the second channel can detect and show features that incorporate the second and/or third nucleotide type (e.g. C and/or T). Unambiguous identification of the nucleotide type incorporated at each feature can be determined, for example, by comparing the two images to arrive at the following: features that show up (i.e., are detected) maximally in the first channel incorporating the first nucleotide type (e.g. A), features that show up maximally in the second channel incorporating the second nucleotide type (e.g. C), features that show up in both channels incorporating the third nucleotide type (e.g. T) and features that don't show up, or are minimally detectable, in either channel incorporating the fourth nucleotide type (e.g. G).

Alternatively, the incorporation of the four nucleotides can be determined using only one combined imaging event. For example, incorporation of the labelled nucleotide types can be determined by exposing the incorporated nucleotides to two excitation wavelengths at one time (e.g., simultaneously) and capturing the emission spectra in one combined image. Unambiguous identification of the incorporated nucleotide types could be determined as previously stated; features that show up in one channel of the combined image would indicate the incorporation of that labelled nucleotide type (e.g., A), features that show up in the second channel of the combined image would indicate the incorporation of that labelled nucleotide type (e.g., C) and features that show up in both channels would indicate the incorporation of a third nucleotide type (e.g., T). As one of the nucleotide types is not labelled (e.g., G) incorporation is determined by absence of, or minimally measurable, features in both channels for that unlabelled nucleotide. Note that the location of the features that incorporate G in this example can be determined from other cycles (where at least one of the other three nucleotide types is incorporated).

In one embodiment of the present disclosure, methods are provided for determining the sequence of a polynucleotide comprising detecting in a sequencing reaction the incorporation of three different types of detectable nucleotide conjugates into a polynucleotide and determining the incorporation of a fourth type of nucleotide based on the detection pattern of the three different types of detectable nucleotides into the polynucleotide thereby determining the sequence of a polynucleotide, wherein the incorporation of three different types of detectable nucleotide conjugates is detected from a signal state and wherein the incorporation of the fourth type of nucleotide is determined from a dark state.

In another embodiment, the present disclosure provides methods for determining the sequence of a polynucleotide comprising applying to a polynucleotide sample for sequencing a solution comprising four modified nucleotide types wherein three modified nucleotide types are conjugated to one or more detection moieties and one or more linkers positioned between the nucleotide and the one or more detection moieties, and wherein a fourth nucleotide type lacks a detection moiety, detecting a pattern of incorporation of said modified nucleotides in a sequencing reaction thereby capturing a first detectable pattern, applying one or more compositions to the sequencing reaction thereby changing the first detectable pattern, detecting a second detectable pattern, and determining the sequence of the polynucleotide sample based on the detectable patterns.

In some embodiments, the polynucleotide for sequencing comprises one or more of deoxyribonucleic acids, modified deoxyribonucleic acids, ribonucleic acids and modified ribonucleic acids. In some embodiments, the polynucleotide for sequencing is a genomic DNA library preparation. In some embodiments, the nucleotide conjugate comprises nucleotide types selected from the group consisting of dATP, dTTP, dUTP, dCTP, dGTP or non-natural nucleotide analogs thereof. In some embodiments, the non-natural nucleotide analog comprises a reversible terminator moiety and is selected from the group consisting of rbATP, rbTTP, rbCTP, rbUTP and rbGTP. In some embodiments, the nucleotide incorporation is sequence by synthesis, sequence by ligation, and sequence by hybridization or a combination thereof. In some embodiments, the three nucleotide type conjugates are detected by detecting a fluorescent moiety. In some embodiments, the fluorescent moiety is the same for the three nucleotide conjugates whereas in other embodiments the fluorescent moiety is one or more different fluorescent moieties. In some embodiments, the one or more different fluorescent moieties are detected by the same emission filter. In some embodiments, the fluorescent moiety comprises a fluorescent resonance energy transfer system moiety. In some embodiments, the incorporation of the fourth nucleotide is determined by lack of detection. In some embodiments, the detectable nucleic acid conjugates are detected by fluorescence. In some embodiments, the fluorescence is detected by a first and a second imaging event, in further embodiments the first and second imaging events are separated in time. In some embodiments, the first imaging event detects a pattern of fluorescence that is different from the pattern of fluorescence detected by the second imaging event. In some embodiments, the incorporation of one or more nucleotides is determined by the difference in the pattern of fluorescence between the first and second imaging events. In some embodiments, the one or more nucleotide type conjugates further comprise one or more linker sequences, in further embodiments the one or more linker sequences comprise one or more of a cleavable linker and a spacer linker. In some embodiments, the cleavable linker comprises one or more cleavable linkage groups selected from the group consisting of a disulfide, a diol, a diazo, an ester, a sulfone, an azide, an allyl and a silyl ether, whereas in preferred embodiments the cleavable linkage group is a disulfide. In some embodiments, the spacer linker is one or more of polyethylene glycol or concatamers thereof and 2-{2-[3-(2-amino-ethylcarbomyl)-phenoxyl-1-azido-ethoxy}-ethoxy-acetic acid. In some embodiments, the one or more spacer linkers further comprise one or more cleavable linkage groups wherein the cleavable linkage group is selected from the group consisting of a disulfide, a diol, a diazo, an ester, a sulfone, an azide, an allyl and a silyl ether.

In some embodiments, the spacer linker is polyethylene glycol or concatamers thereof whereas in other embodiments the spacer linker is 2-{2-[3-(2-amino-ethylcarbomyl)-phenoxyl-1-azido-ethoxy}-ethoxy-acetic acid. In some embodiments, the one or more nucleotide conjugates comprise a polyethylene glycol linker and a 2-{2-[3-(2-amino-ethylcarbomyl)-phenoxyl-1-azido-ethoxy}-ethoxy-acetic acid linker which may or may not further comprise a hapten and a fluorescent moiety. In some embodiments, the hapten is selected from the group consisting of biotin, digoxigenin and dinitrophenol. In some embodiments, the one or more nucleotide conjugates comprises a streptavidin-fluorescent moiety conjugate whereas in other embodiments, the one or more nucleotide conjugates comprises an anti-hapten antibody-fluorescent moiety conjugate selected from the group consisting of anti-digoxigenin and anti-dinitrophenol. In some embodiments the nucleotide conjugate comprising a polyethylene glycol linker and a 2-{2-[3-(2-amino-ethylcarbomyl)-phenoxyl-1-azido-ethoxy}-ethoxy-acetic acid linker further comprises two fluorescent moieties. In some embodiments, the two fluorescent moieties constitute a fluorescence resonance energy transfer system.

An additional embodiment of the present disclosure provides a composition for sequencing a nucleic acid comprising three modified nucleotide types detectable by a fluorescent moiety and a fourth modified nucleotide type, wherein said fourth modified nucleotide type is not detectable by a fluorescent moiety, and wherein the incorporation of the four modified nucleotide types in the composition into a sequencing reaction is determined by the fluorescent detection of the three detectable modified nucleotide types in the composition. In some embodiments, the compositional nucleic acid comprises DNA from a DNA library preparation. In some embodiments, the modified nucleotide type comprises a reversible terminator moiety and is selected from the group comprising of rbATP, rbTTP, rbUTP, rbCTP and rbGTP. In some embodiments, the sequencing reaction is sequence by synthesis, sequence by ligation or sequence by hybridization. In some embodiments, the fluorescent moiety is the same for the three modified nucleotides. In some embodiments, the fluorescent moiety is one or more different fluorescent moieties which are preferably detected by the same emission filter. In some embodiments, the incorporation of three modified nucleotide types is determined by a first fluorescent imaging pattern and a second fluorescent imaging pattern. In some embodiments, the incorporation of the fourth nucleotide type is determined by the fluorescence imaging patterns of the other three nucleotide types. In some embodiments, the compositions described herein comprising the one or more of the modified nucleotide types further comprise one or more linker sequences. In some embodiments, the one or more linker sequences comprise one or more of a cleavable linker and a spacer linker, wherein the cleavable linker comprises one or more cleavable linkage groups selected from the group consisting of a disulfide, a diol, a diazo, an ester, a sulfone, an azide, an allyl and a silyl ether, preferably the cleavable linkage group is disulfide. In some embodiments, the spacer linker is one or more of polyethylene glycol or concatamers thereof and 2-{2-[3-(2-amino-ethylcarbomyl)-phenoxyl-1-azido-ethoxy}-ethoxy-acetic acid, wherein concatamers of polyethylene glycol include between four and twelve polyethylene glycol molecules are sometime preferred. In some embodiments, the one or more spacer linkers further comprise one or more cleavable linkage groups as previously described. In some embodiments, the one or more of three modified nucleotide types comprise a polyethylene glycol linker and a 2-{2-[3-(2-amino-ethylcarbomyl)-phenoxyl-1-azido-ethoxy}-ethoxy-acetic acid linker, whereas some preferred embodiments further comprise a hapten and a fluorescent moiety. In some embodiments, the hapten is selected from the group consisting of biotin, digoxigenin and dinitrophenol. In some embodiments, the hapten is detected by a hapten binding partner-fluorescent moiety conjugate or an anti-hapten antibody-fluorescent moiety conjugate. In some embodiments, the anti-hapten antibody is selected from anti-digoxigenin and anti-dinitrophenol. In some embodiments, said hapten binding partner is streptavidin. In some embodiments, said modified nucleotide types detectable by a fluorescent moiety are conjugated to one or more of a cleavable linker and a spacer linker or a combination thereof, wherein a linker is conjugated to a fluorescent moiety or a hapten, and wherein a modified nucleotide that is not detectable by a fluorescent moiety is not so conjugated.

An additional embodiment as disclosed herein provides a method for determining a plurality of nucleic acid sequences comprising providing a sample comprising plurality of different nucleic acids, each nucleic acid comprising a template and primer; performing a cycle of a sequencing reaction, wherein the cycle comprises extending the primers for the nucleic acids in the sample to form a plurality of extended primers having at least four different nucleotide types, thereby forming an extended sample, acquiring a first collection of signals from the extended sample, wherein no more than three of the different nucleotide types in the extended primers are in a signal state and wherein at least one of the different nucleotide types in the extended primers is in a dark state; treating the extended sample with a modifying reagent, wherein at least one of the different nucleotide types in the extended primers is modified, thereby producing a modified sample, and acquiring a second collection of signals from the modified sample, wherein at least one of the different nucleotide types is in different state in the first collection of signals compared to the second collection of signals; and determining sequences for the plurality of different nucleic acids by evaluating the first collection of signals and the second collection of signals from the cycles. In some embodiments, the plurality of different nucleic acids is attached to a substrate. In some embodiments, the extending of the primers comprises polymerase catalyzed addition of the different nucleotide types. In some embodiments, the different nucleotide types comprise reversible blocking moieties, whereby a single nucleotide type is added to each of the extended primers in each of the cycles. In some embodiments, the extending of the primers comprises ligase catalyzed addition of oligonucleotides comprising the different nucleotide types. In some embodiments, no more than two of the different nucleotide types in the extended primers are in a signal state during the acquiring of the first collection of signals from the extended sample, whereas in other embodiments at least two of the different nucleotide types in the extended primers are in a dark state during the acquiring of the first collection of signals from the extended sample. In some embodiments one of the different nucleotide types in the extended primers is in a dark state during the acquiring of the first collection of signals from the extended sample. In some embodiments, the treating of the extended sample with a modifying reagent comprises removing a label from a nucleotide type or adding a label to a nucleotide type. In some embodiments, at least two of the different nucleotide types in the extended primers is modified by the treating of the extended sample with a modifying reagent, whereas in other embodiments no more than 3 of the different nucleotide types in the extended primers are modified by the treating of the extended sample with a modifying reagent. In some embodiments the extending of the primers for the nucleic acids in the sample forms a plurality of extended primers having no more than four different nucleotide types, whereas in other embodiments the extending of the primers for the nucleic acids in the sample forms a plurality of extended primers having at least five different nucleotide types. In some embodiments, two of the different nucleotide types complement the same nucleotide in the nucleic acid and wherein a first of the two different nucleotide types is in a signal state during the acquiring of the first collection of signals and wherein a second of the two different nucleotide types is in a dark state during the acquiring of the first collection of signals. In some embodiments, the first of the two different nucleotide types is in a dark state during the acquiring of the second collection of signals. In some embodiments, the second of the two different nucleotide types is in a signal state during the acquiring of the second collection of signals. In preferred embodiments, a sequencing reaction cycle as previously described is repeated one or more times.

In another embodiment, the present disclosure provides a method for determining the sequence of a polynucleotide comprising detecting by imaging events the incorporation of three different types of detectable nucleotide conjugates into a polynucleotide and determining the incorporation of a fourth type of nucleotide based on the detection pattern of the three different types of detectable nucleotides into the polynucleotide, wherein detecting comprises fewer imaging events than different types of detectable nucleotide conjugates. In some embodiments, the polynucleotide comprises one or more of deoxyribonucleic acids, modified deoxyribonucleic acids, ribonucleic acids or modified ribonucleic acids. In some embodiments, the nucleotide conjugate comprises nucleotide types selected from the group consisting of dATP, dTTP, dUTP, dCTP, dGTP or non-natural nucleotide analogs thereof wherein the non-natural nucleotide analog comprises a reversible terminator moiety and is selected from the group consisting of rbATP, rbTTP, rbCTP, rbUTP and rbGTP. In some embodiments, the nucleotide incorporation is sequence by synthesis, sequence by ligation or sequence by hybridization. In some embodiments, the three nucleotide type conjugates are detected by detecting a fluorescent moiety, wherein the fluorescent moiety is the same for the three nucleotide conjugates or wherein the fluorescent moiety is one or more different fluorescent moieties. In some embodiments, one or more different fluorescent moieties are detected by the same emission filter. In some embodiments, the fluorescent moiety comprises a fluorescent resonance energy transfer system moiety. In some embodiments, the incorporation of the fourth nucleotide is determined by lack of detection. In some embodiments, the detectable nucleic acid conjugates are detected by fluorescence wherein the fluorescence is detected by the imaging events. In some embodiments, the imaging events comprise a first and a second imaging event for example which are separated in time. In some embodiments, the first imaging event detects a pattern of fluorescence that is different from the pattern of fluorescence detected by the second imaging event. In some embodiments, the incorporation of one or more nucleotides is determined by the difference in the pattern of fluorescence between the first and second imaging events. In some embodiments, the one or more nucleotide type conjugates further comprise one or more linker sequences comprising one or more of a cleavable linker and a spacer linker. In some embodiments, the cleavable linker comprises one or more cleavable linkage groups selected from the group consisting of a disulfide, a diol, a diazo, an ester, a sulfone, an azide, an allyl and a silyl ether, preferably the cleavable linkage group is a disulfide. In some embodiments, the spacer linker is one or more of polyethylene glycol or concatamers thereof and 2-{2-[3-(2-amino-ethylcarbomyl)-phenoxyl-1-azido-ethoxy}-ethoxy-acetic acid. In some embodiments, the one or more spacer linkers further comprise one or more cleavable linkage groups wherein the cleavable linkage group is selected from the group consisting of a disulfide, a diol, a diazo, an ester, a sulfone, an azide, an allyl and a silyl ether. In some embodiments, the spacer linker is polyethylene glycol or concatamers thereof or 2-{2-[3-(2-amino-ethylcarbomyl)-phenoxyl-1-azido-ethoxy}-ethoxy-acetic acid or both. In some embodiments, the nucleotide conjugate comprising a polyethylene glycol linker and a 2-{2-[3-(2-amino-ethylcarbomyl)-phenoxyl-1-azido-ethoxy}-ethoxy-acetic acid linker further comprises a hapten and a fluorescent moiety wherein the hapten is selected from the group consisting of biotin, digoxigenin and dinitrophenol. In some embodiments, the one or more nucleotide conjugates comprises a streptavidin-fluorescent moiety conjugate. In some embodiments, the one or more nucleotide conjugates comprises an anti-hapten antibody-fluorescent moiety conjugate selected from the group consisting of anti-digoxigenin and anti-dinitrophenol. In some embodiments, the nucleotide conjugate comprising a polyethylene glycol linker and a 2-{2-[3-(2-amino-ethylcarbomyl)-phenoxyl-1-azido-ethoxy}-ethoxy-acetic acid linker further comprises two fluorescent moieties. In some embodiments, the two fluorescent moieties constitute a fluorescence resonance energy transfer system. In some embodiments, the one or more nucleotide conjugates further comprise a hapten or a fluorescent moiety, wherein the hapten is selected from the group consisting of biotin, digoxigenin and dinitrophenol. In some embodiments, the one or more nucleotide conjugates comprises a streptavidin-fluorescent moiety conjugate. In some embodiments, the detecting one or more nucleotide conjugates comprises an anti-hapten antibody-fluorescent moiety conjugate selected from the group consisting of anti-digoxigenin and anti-dinitrophenol.

FIGURES

FIG. 1 shows exemplary cloud type heat maps, or cloud plots, for cycles in a sequencing reaction. The plots represent the composite of image 1 (x axis) and image 2 (y axis), such that the plots represent the fluorescence image after a complete cycle. The location of A, C, G and T in the cloud plot is demonstrated in the bottom cloud plot map.

using only one dye, and D) a cloud plot combining the first and second imaging events from a sequencing reaction wherein only one dye and two imaging events are used to differentiate between the four different nucleotides present for incorporation during a sequencing reaction.

Figure 6:
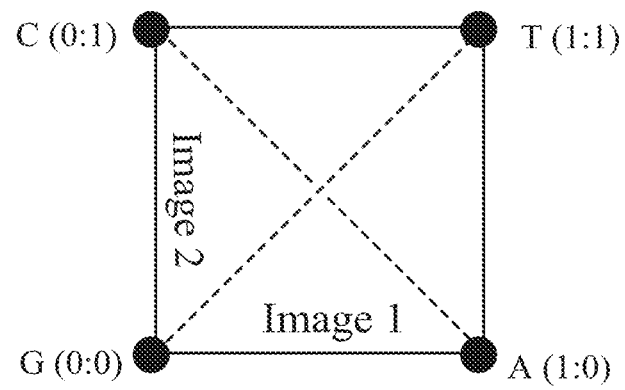
Figure 7:
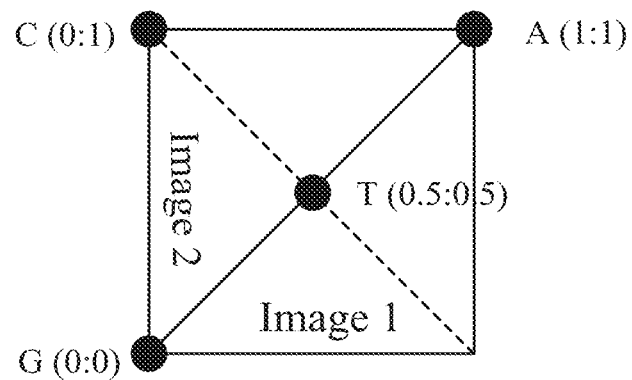
Figure 8:
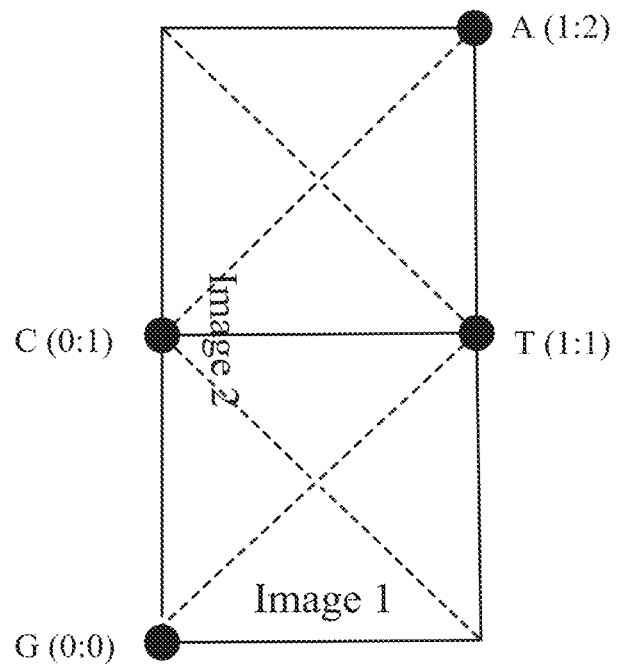

FIGS. 6-8 show grids and tables illustrating alternative strategies for detecting and determining nucleotide incorporation in a sequencing reaction using one fluorescent dye (or two dyes of same or similar excitation/emission spectra) and two imaging steps.

Figure 9:
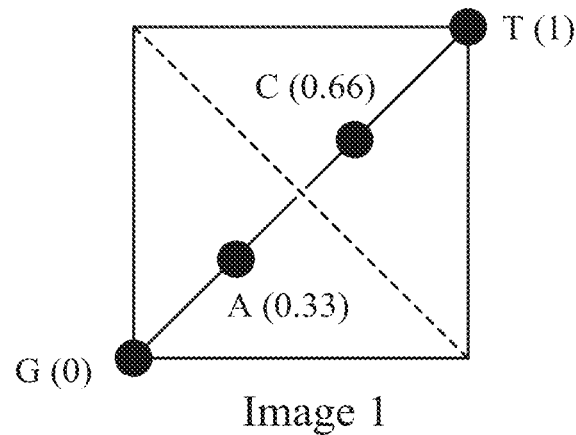
Figure 10:
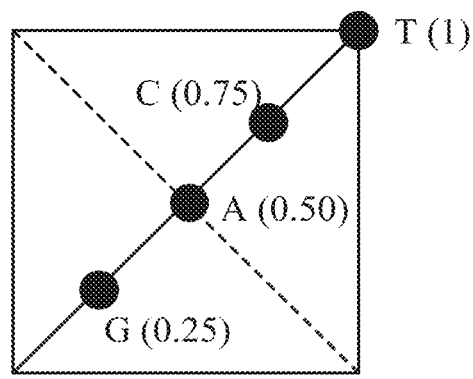

FIGS. 9 and 10 depict grids and tables illustrating alternative strategies for detecting and determining nucleotide incorporation in a sequencing reaction using one fluorescent dye (or two dyes of same or similar excitation/emission spectra) and one imaging step.

Figure 11:
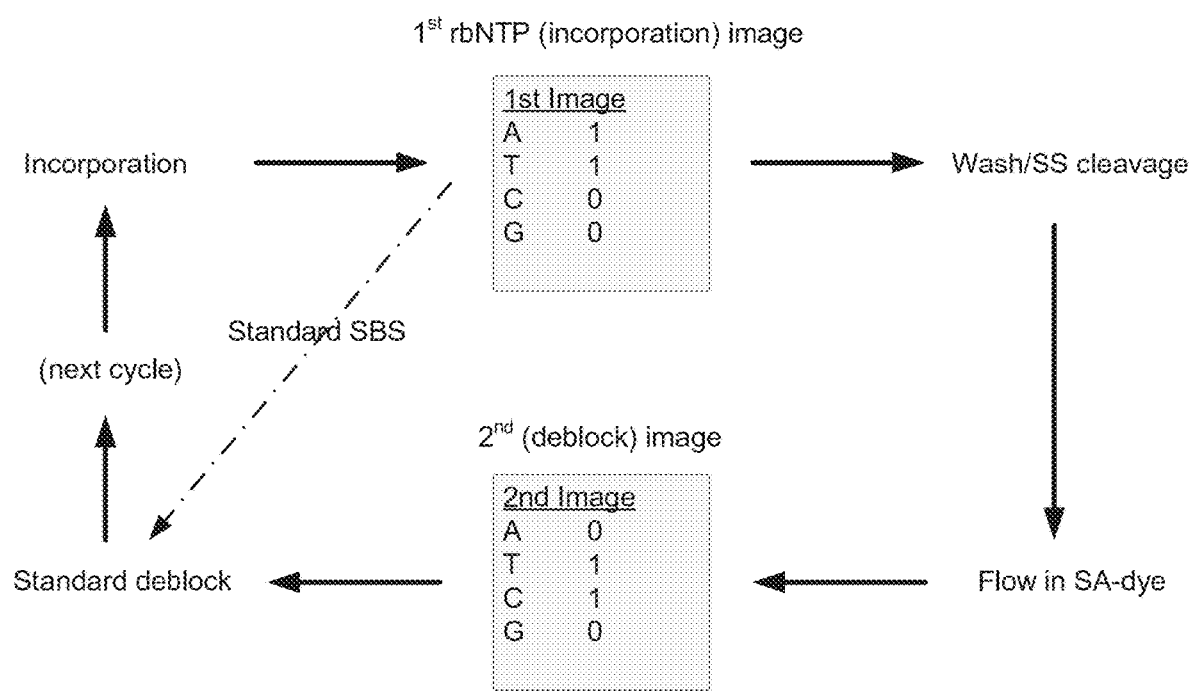
Figure 12:
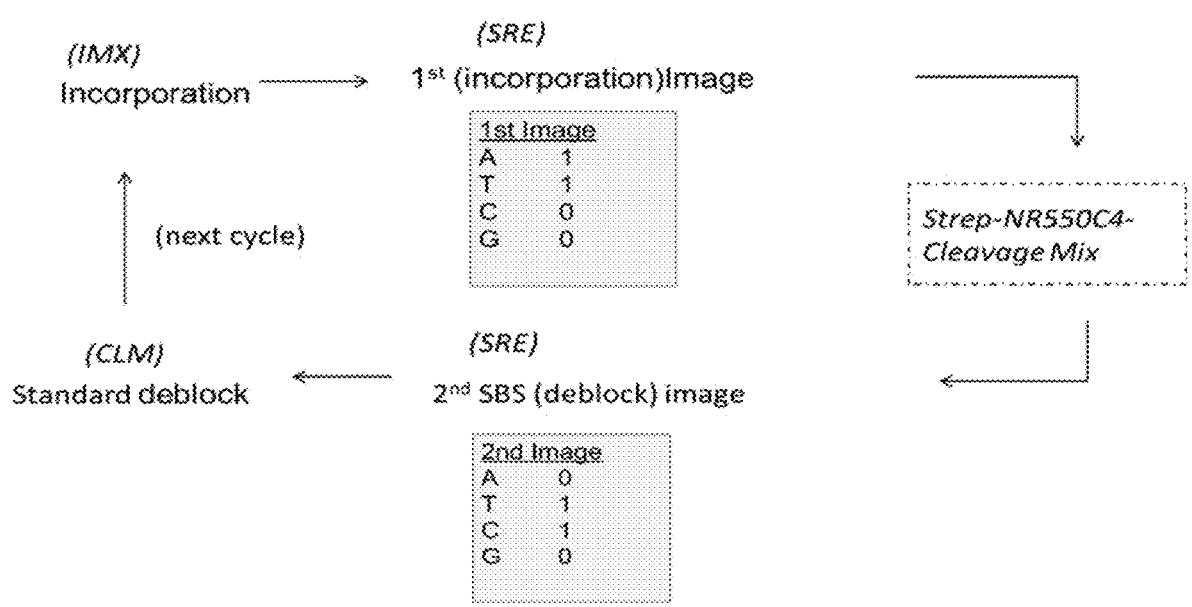

FIGS. 11 and 12 illustrate two exemplary sequencing work flows according to the present invention.

DETAILED DESCRIPTION

Current fluorescence based technologies utilized for differentiating between different analytes in a sample, such as found in sequencing technologies (i.e., fluorescence sequencing technologies) are predicated on, for example, the quality of a signal as generated by a detection moiety that is associated with a particular type of nucleotide. For example, traditional fluorescent sequencing technologies utilize identifiably distinct fluorescent moieties, each attached to one of the four nucleotides A, T, C and G that are utilized in a sequencing reaction. Fluorescently labelled nucleotides utilized during a sequencing reaction, regardless of their method of utilization, are typically excited and measured by one of four optical filters (i.e., one for each distinct dye) in a fluorescent sequencing instrument. Sequence by synthesis (SBS) technology as well as dye terminator sequencing technology utilizing dideoxynucleotides, are exemplary of four channel fluorescence based sequencing technologies. Fluorescence based sequencing instrumentation is typically large, expensive and unattractive to smaller and more capital constrained milieus. New sequencing technologies typically utilize innovative methods, systems and compositions in order to move forward in becoming more accurate (i.e., fewer errors), having higher throughput capacity (i.e., more genomes sequences per given time period) and/or reducing costs (i.e., <$10,000/genome), and desirably have a footprint not to exceed a small space on an investigator's benchtop.

The present disclosure provides solutions for advancing the field of nucleic acid sequencing. Embodiments disclose methods and compositions that utilize minimal detection moieties, for example preferably one dye, or a plurality of dyes with similar detection characteristics, when detecting and differentiating multiple different analytes, such as different nucleotide types, in a sample, for example for sample sequencing. Further, the present disclosure provides methods for determining the incorporation of four nucleotides into a sequencing reaction using less than four detection filters and fewer imaging steps. The use of less than four filters and hence fewer imaging steps allows for sequencing to be performed on smaller formats since fewer excitation and emission filters need to be present. It is contemplated that the methods and systems as described herein decrease instrument hardware needs, decrease the size of an instrument, reagent usage and costs while increasing data output.

In particular embodiments, methods are provided for determining a sequence of monomeric subunits in a polymer. The methods are exemplified herein with regard to nucleic acid polymers and their nucleotide subunits, but can be carried out for other polymers and their subunits. Although the methods can be used for samples having a single polymer sequence, the methods provide particular advantages when used to distinguish several different subunit types in a sample having polymers with many different sequences (i.e. a multiplex polymer sample). For example, in some embodiments the methods provide the ability to distinguish a number of different subunit types in a sample that is greater than the number of different signal types that are acquired from the sample. In the case of a nucleic acid sample, a data acquisition step can be performed on the sample to acquire a collection of less than four different signal types and yet the sequence location for all four of the different nucleotide types can be determined for the sample.

Several aspects of the methods, individually or in combination, provide the ability to distinguish a number of different subunit types (e.g., different nucleotide types, different dideoxynucleotide types, modified dideoxynucleotide types, reversibly bound modified nucleotide types, etc.) in a polymer sample that is greater than the number of different signal types acquired from the polymer sample. The aspects can include, but are not limited to, correlating one or more monomeric subunit type to a dark state, correlating one or more monomeric subunit type to a signal state, correlating one or more monomeric subunit type to a grey state, or correlating one or more monomeric subunit type to a change in state between a dark state, grey state or signal state. A "signal state," when used in reference to a detection event, means a condition in which a specific signal is produced in the detection event. For example, a nucleotide subunit can be in a signal state and detectable when attached to a fluorescent label that is detected in a fluorescence detection step by excitation and emission of that fluorescent label in a sequencing method. The term "dark state," when used in reference to a detection event, means a condition in which a specific signal is not produced in the detection event. For example, a nucleotide subunit can be in a dark state when the nucleotide lacks a fluorescent label and/or does not emit fluorescence that is specifically detected in a fluorescent detection step of a sequencing method. Dark state detection may also include any background fluorescence which may be present absent a fluorescent label. For example, some reaction components may demonstrate minimal fluorescence when excited at certain wavelengths. As such, even though there is not a fluorescent moiety present there may be background fluorescence from such components. Further, background fluorescence may be due to light scatter, for example from adjacent sequencing reactions, which may be detected by a detector. As such, "dark state" can include such background fluorescence as when a fluorescent moiety is not specifically included, such as when a nucleotide lacking a fluorescent label is utilized in methods described herein. However, such background fluorescence is contemplated to be differentiatable from a signal state and as such nucleotide incorporation of an unlabelled nucleotide (or "dark" nucleotide) is still discernible. The term "grey state," when used in reference to a detection event, means a condition in which an attenuated signal is produced in the detection event. For example, a population of nucleotides of a particular type can be in a grey state when a first subpopulation of the nucleotides attached to a fluorescent label that is detected in a fluorescence detection step of a sequencing method while a second subpopulation of the nucleotides lacks the fluorescent label and does not emit fluorescence that is specifically detected in the fluorescent detection step.

In particular embodiments, a method for sequencing a polymer is carried out in cycles, wherein an individual cycle includes one or more steps used to distinguish a monomer at a particular position in the polymer. A cycle can comprise a detection event in some embodiments. However, a sequencing cycle need not include a detection event, for example, if detection is carried out after steps are carried out to distinguish one or more monomers in a polymer. For example, a detection event can occur halfway through a cycle, at the end of one cycle, at the end of 1½ cycles, at the end of two cycles, at the end of 2½ cycles, at the end of three cycles, etc. A further aspect of the methods that can provide the ability to distinguish a number of different subunit types in a polymer sample that is greater than the number of different signal types acquired from the polymer sample, is the use of two or more signal acquisition steps and at least one nucleotide modification step during an individual sequencing cycle. As such, a sequencing method can include several cycles of nucleotide addition and the cycles can include orthogonal steps of acquiring signals from the sequencing sample, then modifying one or more nucleotides in the sequencing sample to change their state (e.g. between a signal state, dark state or grey state), and then acquiring a second set of signals from the sequencing sample. Several examples are set forth in further detail below in which particular nucleotide types are in a signal state due to an attached fluorescent label, particular nucleotide types are in a dark state due to the absence of the label, particular nucleotides are converted from a signal state to a dark state by cleaving a linker that attaches a fluorescent label and/or particular nucleotides are converted from a dark state to a signal state by binding a receptor (e.g. antibody or streptavidin) that recruits a fluorescent label to the nucleotide that did not otherwise have the label.

In lieu of detecting differences in the quality of a fluorescent signal, for example as practiced for some fluorescent sequencing technologies, the present disclosure provides for detection of multiple different analytes (i.e., nucleotides, proteins, or fragments thereof) in a reaction by distinguishing between differences in detection of one fluorescent moiety, or two fluorescent moieties of same or similar excitation/emission spectra (i.e., excited by same laser and emission captured by same optical filter), at different times during a reaction, for example pre and post a change in reaction conditions. In some embodiments, methods for detecting and determining an analyte comprises detecting fluorescence output at two different times during a reaction cycle.

Typically, a reaction cycle will be carried out by delivering at least four nucleotide types to a nucleic acid sample in the presence of a polymerase, for example a DNA or RNA polymerase, during a primer extension reaction. The presence of at least four nucleotide types provides an advantage of increasing polymerase fidelity compared to the use of fewer than four nucleotide types. The use of orthogonal steps to convert one or more incorporated nucleotide types from one state to another state allows multiple nucleotide types to be present simultaneously during a polymerase extension reaction, thereby increasing fidelity while also allowing a single label type to be detected in each cycle, which serves to provide more simplified optics. Use of simplified optics is preferential as compared to systems that rely on more complex optics to record output from multiple different labels to distinguish different nucleotide types that are present simultaneously in an extension reaction. It is further contemplated that in some embodiments fewer that four different types of nucleotides can be present during a polymerase extension reaction.

Certain illustrative embodiments are described below. The compositions and their methods of use are not limited to these embodiments.

In some embodiments, methods for sequencing a nucleic acid comprise the use of one fluorescent moiety for direct or indirect detection of three different nucleotide types and one nucleotide type that is not detected by the presence of a fluorescent signal but is instead detected by a lack or absence of a fluorescent signal. In some embodiments, methods for sequencing a nucleic acid comprise the use of two or more different fluorescent moieties that comprise the same or similar excitation/emission spectra for direct or indirect detection of three different nucleotide types and one nucleotide type that is not detected by the presence of a fluorescent signal but is instead detected by a lack or absence of fluorescent signal. The same or similar excitation and emission spectra are such that a laser excites the two or more different fluorescent moieties and an optical filter captures their emitted fluorescence signals. Detection of fluorescence to determine the sequence of a nucleic acid sample is performed in time space, for example at different times during a sequencing reaction (i.e., pre and post a change in reaction conditions such as enzymatic cleavage, change in environmental pH, addition of additional reagents), providing patterns of fluorescence such as fluorescence transitions patterns, their cumulative patterns determining the sequence of the nucleic acid target. As such, the methods described herein are time and cost efficient and allow for simplification of associated sequencing instrumentation.

An exemplary application of utilizing time space fluorescence pattern differences for determining a target nucleic acid sequence is sequence by synthesis (SBS) methodologies and technologies. As such, embodiments as described herein find particular utility in sequence by synthesis fluorescent applications. Even though embodiments as described herein are exemplary of innovative methods of fluorescent sequencing, the disclosed embodiments also find utility for a variety of other applications where detection of more than one analyte (i.e., nucleotide, protein, or fragments thereof) in a sample is desired.

In developing embodiments for sequencing using a minimal dye set, experimentation revealed alternative strategies for distinguishing between nucleotide incorporations using only one or two fluorescent moieties. These strategies provide for all four nucleotide types to be simultaneously present in a sequence cycle, and for the use of minimal dyes and optical filter sets. In some embodiments, no more than three fluorescent moieties are utilized to determine the incorporation of all four nucleotide types that are present during a reaction, using one or two excitation and emission filters. In preferred embodiments no more than one fluorescent moiety (or two or three of same or similar excitation/emission spectra) is utilized to determine the incorporation of all four nucleotide types that are all present during a reaction, using one excitation range of light and one detection emission filter. It will be understood that, in some embodiments, more than one fluorescent moiety (or moieties of more than one excitation range or emission range) can be used.

In some embodiments, sequencing using a minimal dye set is performed on a substrate, such as a glass, plastic, semiconductor chip or composite derived substrate. In some embodiments, one nucleic acid species is provided on a substrate for example for single target sequencing. In other embodiments, sequencing can also be in a multiplex format, wherein multiple nucleic acid targets are detected and sequenced in parallel, for example in a flowcell or array type of format. Embodiments described herein are particularly advantageous when practicing parallel sequencing or massive parallel sequencing. Platforms practicing fluorescent parallel sequencing include, but are not limited to, those offered by Illumina, Inc. (e.g., HiSeq, Genome Analyzer, MiSeq, iScan platforms), Life Technologies (e.g., SOLiD), Helicos Biosciences (e.g., Heliscope), 454/Roche Life Sciences (Branford, CT) and Pacific Biosciences (e.g., SMART). Flowcells, chips, and other types of surfaces that may accommodate multiple nucleic acid species are exemplary of substrates utilized for parallel sequencing. In multiplex formats wherein multiple nucleic acid species are sequenced in parallel, clonally amplified target sequences (e.g., via emulsion PCR (emPCR) or bridge amplification) are typically covalently immobilized on a substrate. For example, when practicing emulsion PCR the target of interest is immobilized on a bead, whereas clonally amplified targets are immobilized in channels of a flowcell or specific locations on an array or chip.

Flowcells for use with compositions and methods as described herein can be used in sequencing in a number of ways. For example, a DNA sample such as a DNA library can be applied to a flowcell or fluidic device comprising one or more etched flow channels, wherein the flowcell can further comprise a population of probe molecules covalently attached to its surface. The probes attached in the flowcell channels are advantageously located at different addressable locations in the channel and DNA library molecules can be added to the flowcell channels wherein complementary sequences can bind (as described herein, further as described in provisional U.S. Patent Application 61/431,425 which is incorporated herein by reference in its entirety). Another example of a flowcell for use in the present application comprises a CMOS flowcell as described in provisional U.S. Patent Application 61/625,051 which is incorporated herein by reference in its entirety. Bridge amplification can be performed as described herein followed by sequencing by synthesis methods and compositions as described herein. Methods for creating and utilizing flowcells for sequencing are known in the art; references to which are provided herein and all of which are incorporated herein by reference in their entireties. It is contemplated that the methods and compositions as described herein are not limited to any particular manufacture or method of flowcell directed sequencing methodologies.

Sequencing utilizing the methods and compositions described herein can also be performed in a microtiter plate, for example in high density reaction plates or slides (Margulies et al., 2005, Nature 437(7057): 376-380, incorporated herein by reference in its entirety). For example, genomic targets can be prepared by emPCR technologies. Reaction plates or slides can be created from fiber optic material capable of capturing and recording light generated from a reaction, for example from a fluorescent or luminescent reaction. The core material can be etched to provide discrete reaction wells capable of holding at least one emPCR reaction bead. Such slides/plates can contain over a 1.6 million wells. The created slides/plates can be loaded with the target sequencing reaction emPCR beads and mounted to an instrument where the sequencing reagents are provided and sequencing occurs.

An example of arrayed substrates for sequencing targets utilizing compositions and methods as disclosed herein is provided when practicing patterned substrates comprising DNA nanoballs on a chip or slide as performed by Complete Genomics (Mountain View, CA). As described in Drmanac et al., 2010, Science 327(5961): 78-81, a silicon wafer can be layered with silicon dioxide and titanium and subsequently patterned using photolithography and dry etching techniques. The wafer can be treated with HMDS and coated with a photoresist layer to define discrete regions for silanization and subsequent covalent attachment of DNA nanoballs for sequencing. A skilled artisan will appreciate that many methods exist for creating slides/chips with discrete locations for immobilization of nucleic acids for use in sequencing methodologies and the present methods are not limited by the method in which a substrate is prepared for sequencing.

For purposes of illustration and not intended to limit embodiments as described herein, a general strategy sequencing cycle can be described by a sequence of steps. The following example is based on a sequence by synthesis sequencing reaction, however the methods as described herein as not limited to any particular sequencing reaction methodology.

The four nucleotide types A, C, T and G, typically modified nucleotides designed for sequencing reactions such as reversibly blocked (rb) nucleotides (e.g., rbA, rbT, rbC, rbG) wherein three of the four types are fluorescently labelled, are simultaneously added, along with other reaction components, to a location where the template sequence of interest is located and the sequencing reaction occurs (e.g., flowcell, chip, slide, etc.). Following incorporation of a nucleotide into a growing sequence nucleic acid chain based on the target sequence, the reaction is exposed to light and fluorescence is observed and recorded; this constitutes a first imaging event and a first fluorescence detection pattern. Following the first imaging event, one or more additional chemical reagents may be added to the sequencing reaction whereby the added reagent(s) may change the intensity of the fluorescence or some other chemical aspect of the first reaction which causes an identifiable and measurable change in fluorescence (i.e. a fluorescence transition change). The reaction location is once again illuminated and any change in fluorescence is captured and recorded; constituting a second imaging event (i.e., a second fluorescence detection pattern). Blockers present on the incorporated nucleotides are removed and washed away along with other reagents present after the second imaging event in preparation for the next sequencing cycle. Exemplary chemical reagents include, but are not limited to, cleavage reagents, binding partner-fluorescent moiety conjugates, or other reagents that may directly or indirectly cause an identifiable and measurable change in fluorescence from the first imaging event to the second imaging event. The fluorescence patterns from the two imaging events are compared and nucleotide incorporation, and thus the sequence of the target nucleic acid, for that particular cycle is determined. The exemplary general strategy cycle utilizes preferably one fluorescent moiety (or more than one of same or similar excitation/emission) and one emission detection filter to determine incorporation of the four different nucleotide types into a sequencing reaction.

One avenue of differentiating between the different strategies for detecting nucleotide incorporation in a sequencing reaction using one fluorescent dye (or two or more dyes of same or similar excitation/emission spectra) is by characterizing the incorporations in terms of the presence or relative absence, or levels in between, of fluorescence transition that occurs during a sequencing cycle. As such, sequencing strategies can be exemplified by their fluorescent profile for a sequencing cycle. For strategies disclosed herein, "1" and "0" denotes a fluorescent state in which a nucleotide is in a signal state (e.g. detectable by fluorescence) (1) or whether a nucleotide is in a dark state (e.g. not detected or minimally detected at an imaging step) (0). A "0" state does not necessarily refer to a total lack, or absence of signal. Although in some embodiments there may be a total lack or absence of signal (e.g. fluorescence). Minimal or diminished fluorescence signal (e.g. background signal) is also contemplated to be included in the scope of a "0" state as long as a change in fluorescence from the first to the second image (or vice versa) can be reliably distinguished.

Figure 1:
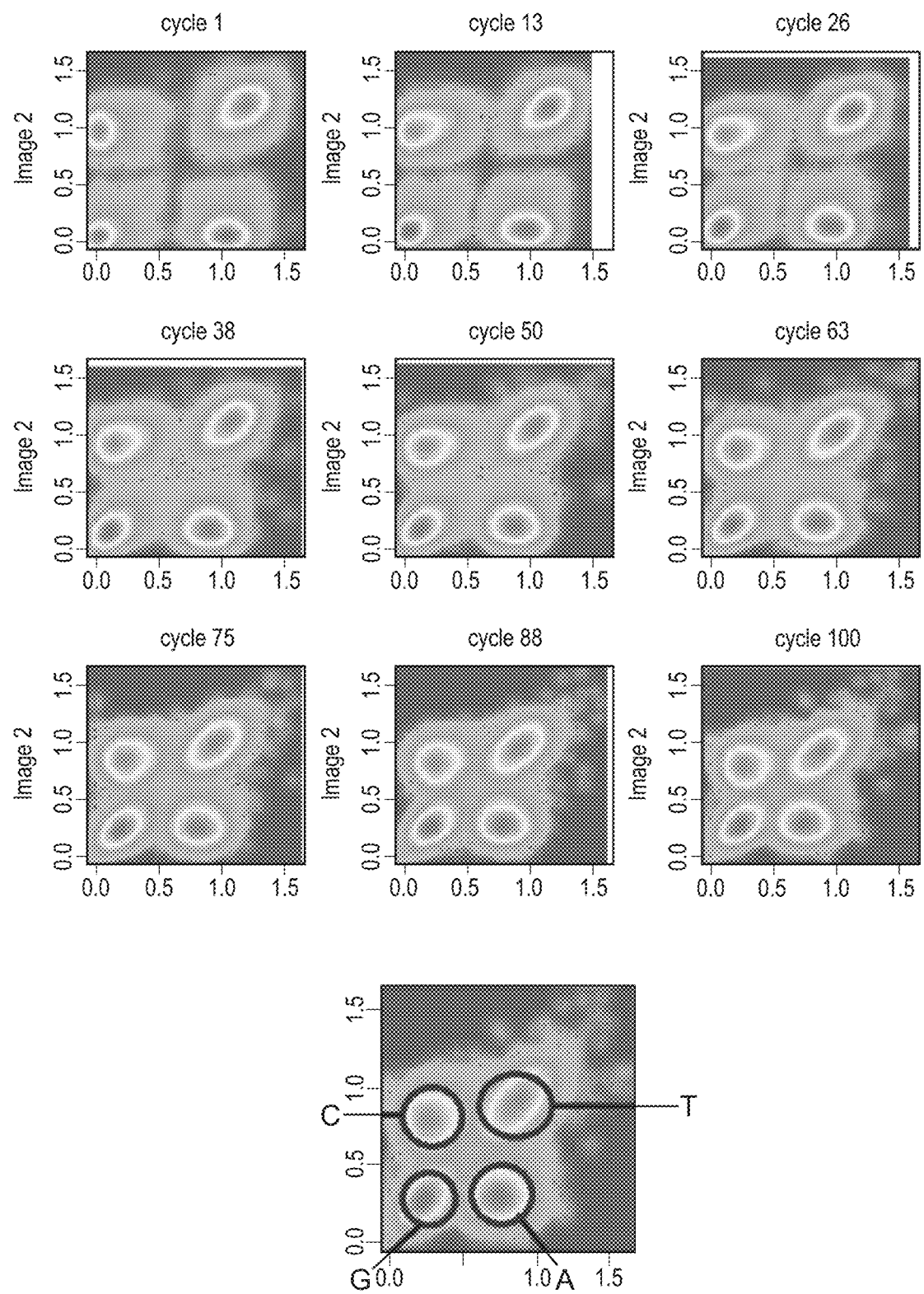

In one embodiment, an exemplary strategy for detecting and determining nucleotide incorporation in a sequencing reaction using one fluorescent dye (or two dyes of same or similar excitation/emission spectra) and two imaging events is exemplified by the grid and detection table shown in FIG. 6. The grid and detection table represent the theoretical space depiction of sequencing data as visualized in the heat map, or cloud plots, for example as seen in FIG. 1.

In some embodiments of sequencing by synthesis (SBS), four modified nucleotide triphosphate types, in this case reversibly blocked nucleotide triphosphates (rbNTPs) are simultaneously added to a SBS reaction. The rbNTPs compete for incorporation into the growing nucleic acid strand during template directed extension of a primer. It is contemplated that competitive extension in the presence of a sufficient variety of nucleotide types to complement all of the nucleotide types in the template nucleic acid improves fidelity of incorporation as compared to adding nucleotides one at a time to a sequencing reaction. The four rbNTP types possess a 3'-terminator that comprises, on the sample 3' ribose position, both alkoxy and azido functionalities which is removable by cleavage with a phosphine reagent, thereby creating a nucleotide that is reversibly blocked and once again functional for further elongation (i.e., fully functional or ff). Fully functional nucleotides, ffNTPs, are commercially available from Illumina, Inc. and are exemplary of reversibly blocked nucleotides, or rbNTPs. In preferred embodiments, three of the four rbNTPs comprise fluorescent labels attached via linkers. The linkers may comprise one or more cleavage groups, or no cleavage groups. For example, a linker attaching one or more rbNTPs to a fluorophore may comprise an azide and/or an alkoxy group, for example on the same carbon, such that the linkers may be cleaved after each incorporation cycle by means of a phosphine reagent as previously referenced, thereby releasing the fluorescent moiety for further sequence elongation.

For example, the initial rbNTP thymine, (rbTTP) may be fluorescently labeled via a linker wherein the linker comprises an azide/alkoxy cleavage site. Another initially fluorescently labeled rbNTP, for example adenine or rbATP, comprises a linker that in addition to the alkoxy/azide group further comprises a second cleavage site like a disulfide group located between, for example, the alkoxy/azide group and the fluorescent label. The fluorescent label associated with rbATP may be the same as the fluorescent label associated with rbTTP, or it may be a similar fluorescent label in that they share similar excitation and emission spectral characteristics. A third rbNTP, for example cytosine or rbCTP, comprises a hapten moiety, such as a biotin, at the terminus of an alkoxy/azide containing linker. In this example the starting rbCTP is not fluorescently labeled and therefore does not fluoresce at a first imaging event. However, subsequent treatment with a fluorescently labeled streptavidin causes binding of the streptavidin-fluorescent moiety conjugate to the biotin moiety on the rbCTP conjugate and after such treatment the locations where rbCTP was incorporated fluoresce when exposed to the appropriate wavelength of light and the fluorescence is recorded during the second imaging event. The fourth rbNTP, in this case guanine or rbGTP lacks a fluorescent moiety and may or may not be conjugated to a linker, is considered a "dark" rbNTP and does not fluoresce, or has diminished or minimal fluorescence, at both imaging events.

The aforementioned exemplary strategy can be further described according to the rbNTP construct, for example:
rbTTP-linker CS1-FM
rbATP-linker CS1-CS2-FM
rbCTP-linker-CS1-B
rbGTP wherein CS1 is a first cleavage site (e.g., azide/alkoxy), CS2 is a second cleavage site (e.g., SS linkage), FM is a fluorescent moiety and B is biotin. It is contemplated that one of the cleavage sites is optional. An optional cleavage site (e.g., two cleavage sites present in a linker) may provide additional functionality to a sequencing cycle including, but not limited to, cleavage of all fluorescent moieties in a subsequent cycle, alternate cleavage reactions in subsequent sequencing cycles and/or combining cleavage reactions in one or more sequencing cycles, or combinations thereof.

An exemplary detection scheme for a sequencing cycle for real time analysis of sequence by synthesis nucleotide incorporation utilizing the aforementioned strategy comprises two imaging event and in particular embodiments no more than two imaging events. The conjugated rbNTPs, rbTTP, rbATP and rbCTP and unconjugated (or perhaps conjugated to linker only) rbGTP are added simultaneously at the beginning of a sequencing cycle. Light of excitation wavelength for the fluorescent moiety is applied to the sequencing reaction and a first image (image 1) is recorded. The first image records fluorescence (1) for rbATP and rbTTP incorporations, but no fluorescence or minimal fluorescence for rbCTP or rbGTP incorporation. Following the first imaging event, DTT for example is added to the reaction which cleaves CS2 (disulfide bond) in the linker of rbATP thereby releasing the FM and transitioning rbATP from detectable (1) to undetectable (0) for the second imaging event. The rbATP cleavage and resulting fluorescent transition step provides for the differentiation of rbATP from the other rbNTP incorporation events during a sequencing cycle. Additionally, following the first imaging step a streptavidin (SA)-FM is added to the reaction. The SA binds the B of the rbCTP composition thereby transitioning rbCTP from undetectable (0) to detectable (1) and allowing for detection of locations where rbCTP was incorporated in the reaction and providing for differentiation of rbCTP incorporation events during a sequencing cycle. In this example, there are no transition changes for either rbTTP or rbGTP. As such, following the application of the exemplary DTT and the SA-FM a second image of the sequencing cycle is taken which results in fluorescent signals for incorporations of rbTTP and rbCTP and no fluorescence for rbATP and rbGTP incorporations. Following the second image the fluorescence transitions, or lack thereof, are used to determine what nucleotide was incorporated at which location in the sequence by synthesis reaction. Each subsequent cycle follows the same pattern of polymerase extension-image 1-chemical treatment-image 2-next cycle until the sequencing run is complete. The cycle can optionally include a nucleotide determination step. Additionally or alternatively, determination of nucleotides or the sequence of nucleotides can occur after one or more cycles are complete. Other steps can also be included per cycle including, but not limited to, deblocking, washing and/or additional steps used in sequence-by-synthesis methods known in the art.

It is contemplated that any number of potential cleavage sites and their cleavage compounds may be utilized in the aforementioned strategy, and those mentioned are by way of example only. For example, reducing agents besides DTT (e.g., TCEP, BME, etc.) or reagents that participate in thiol-disulfide exchange reactions can be used for releasing a fluorescent moiety as described above. Further, hapten binding partners besides biotin-streptavidin (e.g., digoxigenin, dinitrophenol and antibodies thereto) can also be utilized. Further, any one or more fluorescent moieties may be utilized. However if two or more are used it is preferable that they have the same or similar absorption and emission spectra. Preferred embodiments utilize one fluorescent moiety for detection of all incorporated nucleotides, or one optical filter that detects emission from a plurality of fluorescent moieties.

It is contemplated that the reaction reagents (i.e., cleavage reagents, labeling reagents etc.) added between the imaging events can be provided separately, for example sequentially or combined and added as one complete reagent (e.g., a master mix comprising all necessary chemicals to complete cleavage, labeling, etc.). Preferred embodiments comprise addition of a complete reagent solution or master mix between the imaging steps.

In another exemplary embodiment, a second strategy for detecting and determining nucleotide incorporation in a sequencing reaction using one fluorescent dye (or two dyes of same or similar excitation/emission spectra) and two imaging events is exemplified by the detection table and grid shown in FIG. 7.

For the second strategy, as exemplified in the first, all four fully functional nucleotide triphosphate (rbNTPs) compositions are simultaneously added to a SBS reaction. The rbNTPs compete for incorporation into the growing nucleic acid strand. The rbNTPs possess a 3'-terminator that comprises both alkoxy and azido functionalities which are removable by cleavage with a phosphine reagent thereby creating a nucleotide that is once again functional for further elongation. In preferred embodiments, three of the four rbNTPs comprise fluorescent labels attached via linkers. The linkers may comprise one or more cleavage sites. For example, a linker attaching one or more rbNTPs to a fluorophore may comprise an azide and/or an alkoxy group, for example on the same carbon, such that the linkers may be cleaved after each incorporation cycle by means of a phosphine reagent thereby releasing the fluorescent moiety for further sequence elongation.

In the second strategy, the initial pool of rbNTP thymine comprises a mixture of rbTTP molecules. For example, a pool of rbTTP comprises a 2:1 ratio of a fluorescently labeled rbTTP (i.e., via a linker) and non-fluorescently labeled rbTTP (i.e., dark rbTTP). It is contemplated that any ratio of fluorescent:non-fluorescent rbNTP, can be used. For example a 2:1, 1:0.5, 0.5:1, and 1:2 ratios would also work, the difference of which would change the image intensity output without changing the ability to detect and differentiate nucleotide incorporation. A fluorescently labeled rbATP, an unlabeled or dark rbGTP and a biotin labeled rbCTP complete the nucleotide mix. A subsequent treatment with a fluorescently labeled streptavidin causes binding of the streptavidin-fluorophore moiety to the biotin moiety on the rbCTP conjugate and after such treatment the locations where rbCTP was incorporated fluoresce when exposed to the appropriate wavelength of light and the fluorescence is recorded during the second imaging event.

The aforementioned exemplary strategy can comprise the rbNTP constructs:
rbTTP-linker FM/rbTTP-dark
rbATP-linker-FM
rbCTP-linker-B
rbGTP-dark An exemplary detection scheme for a sequencing cycle for real time analysis of sequence by synthesis nucleotide incorporation utilizing the aforementioned strategy comprises two imaging events and in particular embodiments no more than two imaging events. All four of the rbNTP types are added simultaneously at the beginning of a sequencing cycle. Light of excitation wavelength for the fluorescent moiety is applied to the sequencing reaction and a first image (image 1) is recorded. The first image includes fluorescence (1) for rbATP and rbTTP (at 50% fluorescence intensity) incorporations, but no fluorescence for rbCTP, rbGTP and ½ of the rbTTP incorporations. Following the first imaging step, a streptavidin labeled fluorophore SA-FM is added to the reaction. The SA binds the B of the rbCTP composition thereby transitioning rbCTP from undetectable (0) to detectable (1) during the second imaging event and allowing for detection of locations where rbCTP was incorporated in the reaction and providing for differentiation of rbCTP incorporation events during a sequencing cycle. In this example, there are no transition changes for rbTTP, rbATP or rbGTP. Following the second image the fluorescence transitions, or lack thereof, are used to determine what nucleotide was incorporated at which location in the sequence by synthesis reaction and the sequence of interest is identified. Each subsequent cycle follows the same pattern of polymerase extension-image 1-treatment-image 2-next cycle until the total sequencing of the desired target is complete. The cycle can optionally include a nucleotide determination step. Additionally or alternatively, determination of nucleotides or the sequence of nucleotides can occur after one or more cycles are complete. Other steps can also be included per cycle including, but not limited to, deblocking, washing and/or additional steps used in sequence-by-synthesis methods known in the art.

In another embodiment, a third strategy for detecting and determining nucleotide incorporation in a sequencing reaction using one fluorescent dye (or two dyes of same or similar excitation/emission spectra) and two imaging steps is exemplified by the detection table and grid shown in FIG. 8.

As exemplified in the first and second, all four fully functional nucleotide triphosphate (rbNTPs) compositions are simultaneously added to a SBS reaction. The rbNTPs compete for incorporation into the growing nucleic acid strand. The rbNTPs possess a 3'-terminator that is removable, thereby creating a nucleotide that is once again functional for further elongation. The third strategy differs from previous exemplary strategies by incorporating, for example, by conjugating a rbNTP to a branched linker. In preferred embodiments, two of the four rbNTPs comprise fluorescent labels attached via linkers. The linkers may comprise one or more cleavage sites. For example, a linker attaching one or more rbNTPs to a fluorophore may comprise an azide and/or an alkoxy group, for example on the same carbon, such that the linkers may be cleaved after each incorporation cycle by means of a phosphine reagent as previously described, thereby releasing the fluorescent moiety for further sequence elongation.

In the third exemplary strategy, rbATP and rbCTP complexes comprise branched linkers. For example, rbATP comprises a branched linker wherein one branch terminates with a fluorescent moiety and a second branch terminates in a biotin. In this example, the rbCTP is also complexed with a branched linker and each of two branches terminates in a biotin. The rbCTP in this example is initially unlabeled. A fluorescently labeled rbTTP and an unlabeled or dark rbGTP complete the nucleotide mix. A subsequent treatment with a fluorescently labeled streptavidin causes very strong binding of the streptavidin-dye to the biotin moieties on the C and A nucleotides and after such treatment the locations where rbCTP and rbATP were incorporated fluoresce when exposed to the appropriate wavelength of light and the fluorescence resulting from the B-SA interaction is recorded during the second imaging step.

The aforementioned exemplary strategy as such can comprise:
rbATP-branched linker FM and B
rbTTP-FM
rbCTP-branched linker-(B)$^2$
rbGTP-dark An exemplary detection scheme for a sequencing cycle for real time analysis of sequence by synthesis nucleotide incorporation utilizing the aforementioned strategy comprises two imaging steps and in particular embodiments no more than two imaging events. All the rbNTPs are added simultaneously at the beginning of a sequencing cycle. Light of excitation wavelength for the fluorescent moiety is applied to the sequencing reaction and a first image (image 1) is recorded. The first image includes fluorescence (1) for rbATP and rbTTP incorporations, but no fluorescence (0) for rbCTP and rbGTP incorporations. Following the first imaging step, a streptavidin labeled fluorophore SA-FM is added to the reaction. The SA binds the two biotins (B$^2$) of the rbCTP conjugate thereby transitioning rbCTP from undetectable (0) to detectable (1) and the B on the bifurcated linker of rbATP thereby effectively increasing the fluorescence (2) of rbATP incorporation from image 1 and allowing for detection of locations where rbCTP was incorporated, and differentiating rbATP incorporation, in the growing nucleic acid strand. In this example, there are no transition changes for rbTTP or rbGTP. Following the second image the fluorescence transitions, or lack thereof, are used to determine what nucleotide was incorporated at which location in the sequence by synthesis reaction and the sequence of interest is identified. Each subsequent cycle follows the same pattern of polymerase extension-image 1-treatment-image 2-next cycle until sequencing of the desired target is complete. The cycle can optionally include a nucleotide determination step. Additionally or alternatively, determination of nucleotides or the sequence of nucleotides can occur after one or more cycles are complete. Other steps can also be included per cycle including, but not limited to deblocking, washing and/or other steps used in sequence-by-synthesis methods known in the art.

In another embodiment, a fourth exemplary strategy for detecting and determining nucleotide incorporation in a sequencing reaction uses one fluorescent dye (or two dyes of same or similar excitation/emission spectra) and only one imaging step as exemplified by the detection table and grid shown in FIG. 9.

The aforementioned exemplary embodiment can comprise only one dye, or two dyes of the same or similar excitation/emission spectra wherein the dye concentration changes for each of the three labeled rbNTPs. A dark state denotes the incorporation of, in this case, rbGTP based on the interpretation of fluorescence measurement from the three fluorescently labeled rbNTPs.

The aforementioned exemplary strategy as such can comprise:
rbATP-FM (0.33× concentration)
rbTTP-FM (1.0× concentration)
rbCTP-FM (0.66× concentration)
rbGTP-dark An alternative embodiment comprising one dye (or two dyes of the same or similar excitation/emission spectra) and one image event is illustrated in the detection table and grid shown in FIG. 10.

The aforementioned exemplary strategy as such can comprise:
rbATP-FM (0.50× concentration)
rbTTP-FM (1.0× concentration)
rbCTP-FM (0.75× concentration)
rbGTP-FM (0.25× concentration)

The aforementioned exemplary embodiment can comprise one dye or two dyes of similar excitation/emission spectra such that each of the four rbNTPs are labelled with different dye concentrations. In embodiments wherein each of four different rbNTPs are attached to a different concentration of one dye (or two dyes of similar excitation/ emission spectra) only one image is taken per cycle to determine nucleotide incorporation. An exemplary sequence cycle practicing one dye/one image event methods would be polymerase extension-image 1-next cycle.

An exemplary detection scheme for a sequencing cycle for one dye/one image event sequence by synthesis nucleotide incorporation utilizing the aforementioned strategies comprises one imaging step. All the rbNTPs are added simultaneously at the beginning of a sequencing cycle. Light of excitation wavelength for the fluorescent moiety is applied to the sequencing reaction and a first image (image 1) is recorded. Following the first imaging step, the next cycle of reagent addition, polymerase extension and image acquisition are carried out until the desired number of cycles are completed. Following the first image the fluorescence intensity can be correlated to the different dye concentrations are used to determine what nucleotide was incorporated at which location in the sequence by synthesis reaction and the sequence of interest is identified. Each subsequent cycle follows the same pattern of polymerase extension-image 1-next cycle until sequencing of the desired target is complete. The cycle can optionally include a nucleotide determination step. Additionally or alternatively, determination of nucleotides or the sequence of nucleotides can occur after one or more cycles are complete. Other steps can also be included per cycle including, but not limited to deblocking, washing and/or other steps used in sequence-by-synthesis methods known in the art.

In embodiments practicing one dye/one image event sequencing, dye concentrations are provided that allow for the differentiation of incorporation of the labelled and/or unlabelled nucleotides. Further, when practicing a sequencing reaction of one dye/one image as exemplified above, additional chemical treatment is not necessary as previously described for embodiments for one dye/two image sequencing strategies.

In another exemplary embodiment, an additional strategy for detecting and determining nucleotide incorporation in a sequencing reaction comprises using two fluorescent dyes of different excitation and emission spectra and either 1) one imaging event comprising two emission spectra or 2) two sequential imaging events.

Figure 3:
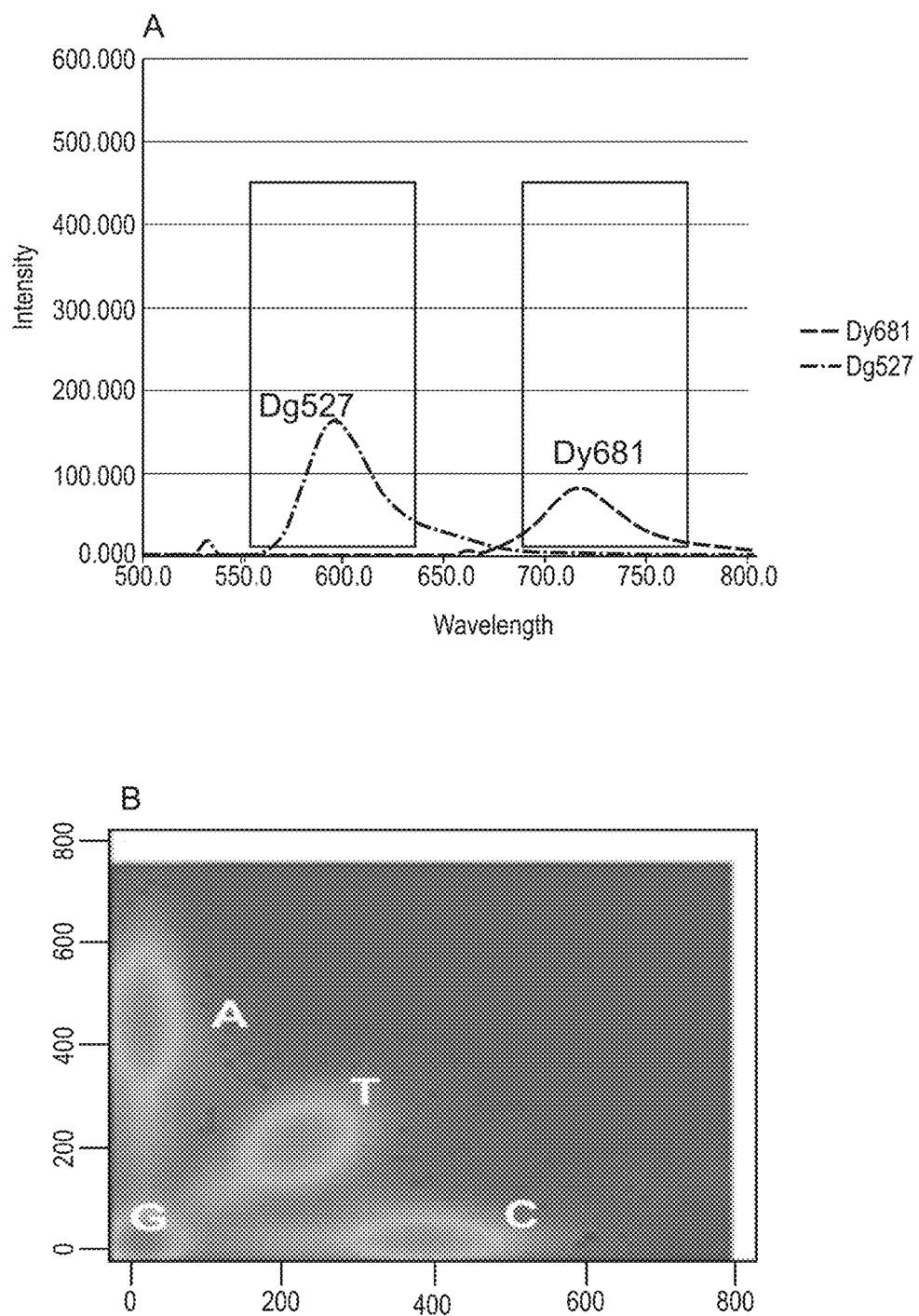
FIG. 3 shows A) emission spectra for two exemplary dyes and B) an exemplary cloud plot for a sequencing cycle when practicing the embodiment of using two dyes of different fluorescence spectra for sequencing.

For purposes of example FIG. 3A shows two exemplary dyes, a dye that emits at around 590$\lambda_{max}$ (DEG527) and a dye that emits at around 720$\lambda_{max}$ (Dy681). For purposes of example, the following rbNTP-dye conjugations are made:
rbATP-DEG527
rbCTP-Dy681
rbTTP-DEG527/Dy681
rbGTP-dark As such, the percentage of each incorporated nucleotide conjugated to a particular fluorophore. In this example the conjugations are:

| rbNTP | Dy681 | DEG527 | Dark |
|---|---|---|---|
| rbATP |  | 100% |  |
| rbCTP | 100% |  |  |
| rbTTP | 50% | 50% |  |
| rbGTP |  |  | 100% |

As an example, following standard SBS protocols, all four of nucleotides are added simultaneously to a SBS reaction. The rbNTPs compete for incorporation in the growing nucleic acid strand. As previously described, the rbNTPs possess a 3' terminator that is removable by cleavage for further elongation. Following incubation allowing for the incorporation of the appropriate nucleotide into the growing nucleic acid strand, the reaction is exposed to the appropriate wavelength of light depending on which imaging, simultaneous or sequential, is desired. For example, the reaction can be exposed simultaneously to the excitation wavelength of both fluorescent dyes (in this example, DEG527 is excited at approximately 532 nm and Dy681 is excited at approximately 660 nm) thereby causing simultaneous emission of the two fluorescent dyes, emission of which can be detected simultaneously by two different detection filters and imaging optics. In such a simultaneous system wherein only 1 imaging event is performed for two different detection channels simultaneously, the image states for each detection channel would be:

|  | Image 1-green | Image 1-red |
|---|---|---|
| A | 1 | 0 |
| C | 0 | 1 |
| T | 0.5 | 0.5 |
| G | 0 | 0 |

Alternatively, after incorporation of the appropriate labeled nucleotide into the growing nucleic acid strand the two fluorescent dyes can be excited in a step by step manner, such as first exciting one fluorophore followed by a first imaging event and then exciting the second fluorophore followed by a second imaging event. In such a step by step imaging system two imaging events are performed and the detection table would be, for example if DEG527 is first excited followed by Dy681 (e.g., vice versa if red fluorescence emission is first imaged followed by green fluorescence) the image states for each image event would be:

|  | Image 1-green | Image 2-red |
|---|---|---|
| A | 1 | 0 |
| C | 0 | 1 |
| T | 0.5 | 0.5 |
| G | 0 | 0 |

In either case, the incorporation of an A would be detected at a certain intensity in the green channel only, the incorporation of a C would be detected at a certain intensity in the red channel only, the incorporation of a T would be detected in both the green and red channels at half the intensity of the A and C, and G would be minimally or not detected in either green or red channels (FIG. 3B). Following the imaging step or steps, the fluorescent dye and the 3' terminator are cleaved and the next sequencing cycle is performed.

This example is not limited to any particular two dyes or conjugate combinations and any two dyes of different fluorescence spectra could be used in a two dye sequencing system, in any combination of rbNTP-dye conjugate combination. For example, the dyes depicted in the above example emitted in the red and green wavelengths. However, the methods and systems are not limited by the excitation or emission wavelengths (e.g., fluorescence spectra) of any particular dye, as such any dyes that differ in fluorescence spectra can be potentially useful. Further, the example describes certain rbNTP-dye conjugates; however conjugates are not limited to those particular combinations. For example, any of three rbNTPs could be potentially conjugated to any of the listed dyes (one nucleotide remaining unconjugated or dark). Examples of dyes and derivatives thereof useful in embodiments described herein include, but are not limited to, those described below.

Additionally, the one or more nucleotide type conjugates described in the above strategy could further comprise one or more linkers as described in alternative embodiments and strategies. As such, one or more chemical or modifying reactions could be incorporated into a sequencing reaction in combination with the strategy wherein two dyes of different fluorescence spectra are conjugated to different nucleotide types. Therefore, the nucleotide type conjugates in this example could be further modified in any number of ways as described herein without detracting from the embodiment wherein two dyes of different fluorescence spectra can be employed to determine the sequence of a nucleic acid.

In another exemplary embodiment, an additional strategy for detecting and determining nucleotide incorporation in a sequencing reaction comprises using two fluorescent dye sets wherein each set of dyes comprises two dyes of similar fluorescence emission spectra or with emission $\lambda_{max}$ off-set by up to, for example, 100 nm, wherein one of the two dyes emits at a detectably higher intensity than the other dye in the set, and wherein the two fluorescent dye sets differ in fluorescence emission spectra. In preferred embodiments, the dye in a dye set that is detectably higher intensity than the other dye in the set is at least 0.5×, at least 0.75×, at least 1×, at least 2× as intense as the lower intensity dye. When practicing two fluorescent dye sets as described herein, sequence determination can be via one imaging event or two imaging events.

Figure 4:
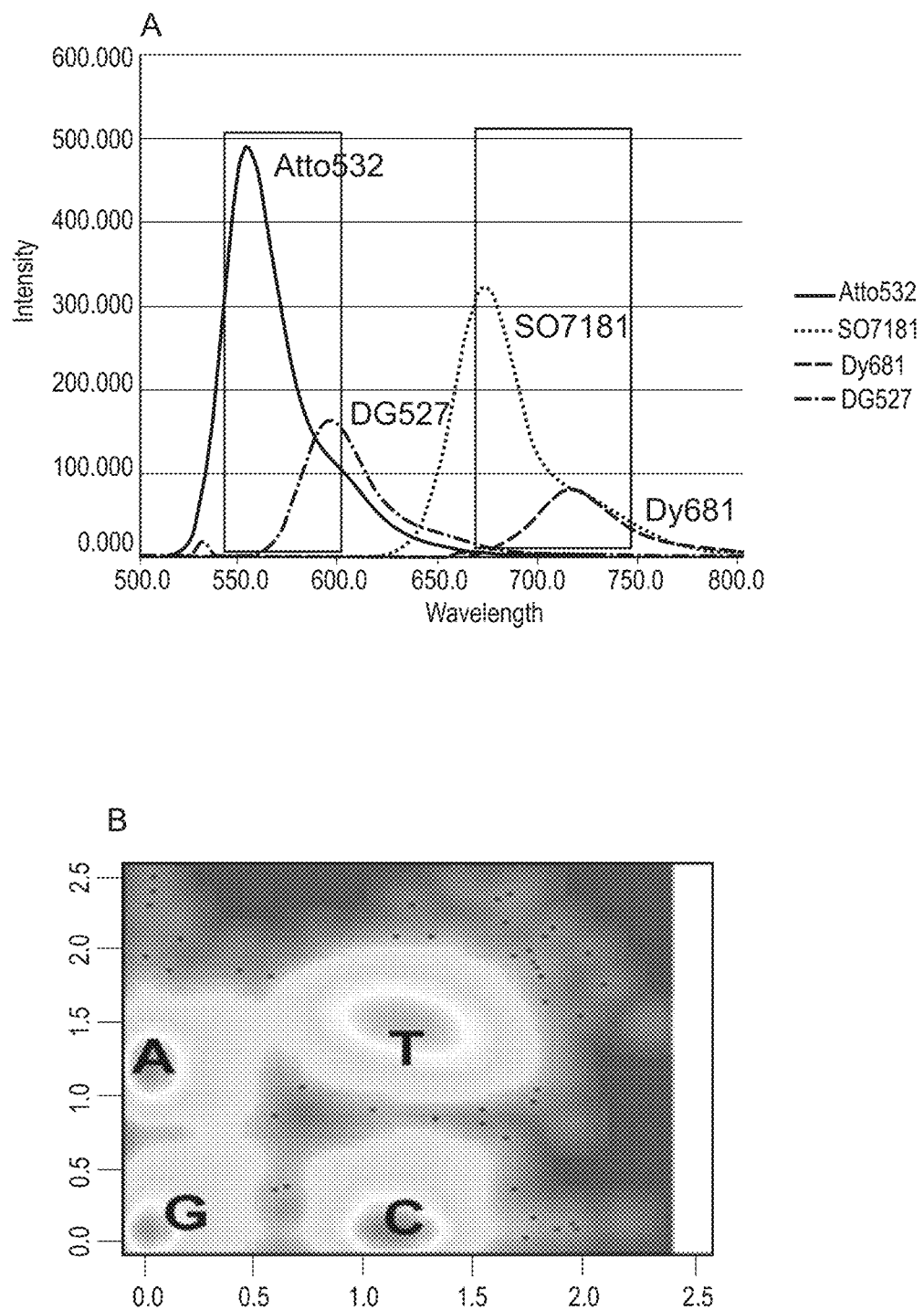
FIG. 4 shows A) emission spectra for two exemplary dye sets and B) an exemplary cloud plot for a sequencing cycle when practicing the embodiment of using two dye sets of different emission spectra for sequencing.

For purposes of example FIG. 4A shows two exemplary dye sets; both DEG527 and Atto532 can be detected together (fluorescence emission from approximately $\lambda_{max}$ 555-595 nm) and Dy681 and SO7181 can be detected together (fluorescence emission from approximately $\lambda_{max}$ 670-715 nm). For purposes of example, the following rbNTP-dye conjugations are made:
rbATP-DEG527
rbCTP-Dy681
rbTTP-Atto532/SO7181
rbGTP-dark As such, the percentage of each incorporated nucleotide conjugated to a particular fluorophore in this example is:

| rbNTP | SO7181 | Dy681 | Atto532 | DEG527 | Dark |
|---|---|---|---|---|---|
| rbATP | | | | 100% | |
| rbCTP | | 100% | | | |
| rbTTP | 50% | | 50% | | |
| rbGTP | | | | | 100% |

As an example, following standard SBS protocols, all four of nucleotides are added simultaneously to a SBS reaction. The rbNTPs compete for incorporation in the growing nucleic acid strand. As previously described, the rbNTPs possess a 3' terminator that is removable by cleavage for further elongation. Following incubation allowing for the incorporation of the appropriate nucleotide into the growing nucleic acid strand, the reaction is exposed to a first wavelength of light, a first imaging event is performed, then the reaction is exposed to the second wavelength of light and a second imaging event is performed.

For example, after incorporation of the appropriate labeled nucleotide into the growing nucleic acid strand the two sets of fluorescent dyes can be excited in a step by step manner, such as first exciting one set of fluorophores followed by a first imaging event and then exciting the second set of fluorophores followed by a second imaging event. As an example, if DEG527/Atto532 is first excited followed by Dy681/SO7181 (e.g., vice versa if red fluorescence emission is first imaged followed by green fluorescence) the image states for each image event would be:

| | Image 1-green | Image 2-red |
|---|---|---|
| A | 1 | 0 |
| C | 0 | 1 |
| T | >1 | >1 |
| G | 0 | 0 |

The image states for T are listed as >1 for each image event. The >1 designation assumes that the higher intensity dye is at least greater in intensity than that of the lower intensity dye in the dye pair.

Alternatively, the reaction can be exposed simultaneously to the excitation wavelength of both fluorescent dyes thereby causing simultaneous emission of the two fluorescent dyes, emission of which can be detected simultaneously by two different detection filters and imaging optics. In such a simultaneous system wherein only 1 imaging event is performed for two different detection channels simultaneously, the image states for each detection channel would be:

| | Image 1-green | Image 1-red |
|---|---|---|
| A | 1 | 0 |
| C | 0 | 1 |
| T | >1 | >1 |
| G | 0 | 0 |

In either case, the incorporation of an A would be detected at a certain intensity in the green channel only and the incorporation of a C would be detected at a certain intensity in the red channel only. However, due to the increased intensity of the dyes that are conjugated to rbTTP compared to the lower intensity dyes conjugated to the rbATP and rbCTP, it is contemplated that the incorporation of a T would be detected in both the green and red channels at equal to or greater intensity of the A and C. Once again, in this example incorporation of G would be minimally or not detected in either green or red channels.

FIG. 4B shows a cloud heat map demonstrating the detection of incorporated rbTTP as compared to rbCTP and rbATP when practicing the described two dye sets, wherein one dye is of higher intensity than the other dye in the set. Following the imaging steps, the fluorescent dye and the 3' terminator are cleaved and the next sequencing cycle is performed.

Additionally, the one or more nucleotide type conjugates described in this example could further comprise one or more linkers as described in alternative embodiments. As such, one or more chemical or modifying reactions could be incorporated into a sequencing reaction in combination with the strategy wherein two dye sets of different emission spectra are conjugated to different nucleotide types. Therefore, the nucleotide type conjugates in this example could be further modified in any number of ways as described herein without detracting from the embodiment wherein two dye sets of different emission spectra can be employed to determine the sequence of a nucleic acid.

Additionally, this example is not limited to any particular two dye sets or conjugate combinations and any two dye sets of different emission spectra could be used, in any combination of rbNTP-dye conjugate combination while following the strategy for conjugation as disclosed herein (e.g., two nucleotide types are conjugated to different lower intensity dyes and one nucleotide type is conjugated to two higher intensity dyes). The example describing the use of two dye sets for sequencing methods is not limited to any particular sets of two dyes and any dye sets of different fluorescence spectra could be used in the sequencing system as described herein. Additional dye sets comprise those that have emission $\lambda_{max}$ off-set of at least 60 nm, at least 70 nm, at least 80 nm, at least 90 nm, at least 100 nm, preferably at least 100 nm. Examples of dye sets include, but are not limited to, Atto465, 488, 495/Atto514, 520, 532, 550, 565; Atto 520, 532, 550/Atto565, 590, 594, Rho11, Rho 12, Rho 13; Atto 647, 655, 665/Atto 680, 700, 725; Alexa 647, 660, Cy5/Alexa 680, 700, Cy5.5; Alexa532, Cy3/Alexa555, 556, 578, 590, Cy3.5; Alexa 488/Alexa532, 555, 556, 578; Dy 647, 648, 649, 650, 651, 652, 654/Dy675, 676, 677, 678, 679, 680, 681, 682, 700, 701, 703, 704; Dy490, 495, 505/Dy530, 547, 548, 549, 550, 554, 555, 556, 560; Dy530, 547, 548, 549, 550, 554, 555, 556, 560/Dy590, 591, 594, 605, 610, 615.

The above strategies are exemplary in nature, describe only several of many potential strategies and serve to provide a guide underlying the innovative methods and compositions disclosed herein for utilizing one fluorescent moiety, or a plurality of fluorescent moieties of the same or similar excitation/emission spectra, for sequencing a nucleic acid. A skilled artisan will understand that the different strategies provide a guide for creating additional strategies using one fluorescent moiety, or a plurality of fluorescent moieties of the same or similar excitation/emission spectra, for sequencing a nucleic acid, and still be within the scope of the methods as disclosed herein.

In one embodiment, a rbNTP conjugate as described herein comprises detection moiety(s) ~~~~ linker(s) ~~~~ base

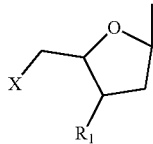

wherein a detection moiety is one or more of a fluorescent moiety, a hapten or combinations thereof, wherein a linker is one or more of a spacer linker, a linker with one or more cleavage sites, or combinations thereof, wherein a base is one of three modified nucleotides (e.g., rbNTPs) wherein X is a monophosphate, diphosphate or triphosphate and wherein $R_1$ is —H, —OH, —OCH2N$_3$ or any group which can be transformed into an —OH, including carbonyl covalently bonded to the 3' carbon.

In some embodiments, a detection moiety is a fluorescent moiety. In some embodiments, a detection moiety is a hapten that is detectable via a binding partner-fluorescent moiety conjugate. In some embodiments, a rbNTP conjugate comprises one or both of a fluorescent moiety and a hapten linked to a rbNTP via one or more linkers. In some embodiments a hapten is a biotin, digoxigenin (DIG) or dinitrophenol (DNP). In some embodiments, a hapten is detected by a binding partner-fluorescent moiety conjugate. In some embodiments, a binding partner is a small molecule or an antibody or fragment thereof, for example streptavidin, anti-DIG or anti DNP.

Exemplary fluorescent moieties, or derivatives thereof, for use as fluorescent moieties in accordance with disclosed embodiments include, but are not limited to, fluorescein and fluorescein derivatives such as carboxyfluorescein, tetrachlorofluorescein, hexachlorofluorescein, carboxynaphthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malacite green, stilbene, DEG dyes (for example as those described in US2010/0009353, incorporated herein by reference in its entirety), NR dyes, near-infrared dyes and others known in the art such as those described in Haugland, Molecular Probes Handbook, (Eugene, OR) 6th Edition; The Synthegen catalog (Houston, TX), Lakowicz, Principles of Fluorescence Spectroscopy, 2nd Ed., Plenum Press New York (1999), Hermanson, Bioconjugate Techniques, $2^{nd}$ Edition, US2010/0009353 or WO 98/59066, each of which is incorporated by reference in their entireties.

In some embodiments, a detection moiety is conjugated to a rbNTP via a linker. In some embodiments a rbNTP conjugate comprises one or more than one linker. In some embodiments, a linker is a spacer linker that is conjugated on one end to a rbNTP and on the other to a detection moiety. In some embodiments, a spacer linker comprises one or more cleavage groups. Conversely, in some embodiments a spacer linker contains no cleavage group. In one embodiment, a spacer linker (e.g., with or without a cleavage group) is a polyethylene glycol (PEG) molecule or concatamers thereof. For example, in some embodiments, a spacer linker comprises concatamers of at least two, of at least three, of at least four, of at least five, of at least six, of at least seven, of at least eight, of at least ten or of at least twelve PEG molecules.

In preferred embodiments, spacer linkers used to conjugate a rbNTP to a detection moiety, for example a fluorescent moiety or a hapten, comprise at least four to twelve concatamers of PEG (i.e., PEG4, PEG 8, PEG 12). In some embodiments, a spacer linker comprises 2-{2-[3-(2-amino-ethylcarbomyl)-phenoxyl-1-azido-ethoxy}-ethoxy-acetic acid. In some embodiments, the spacer linker comprising 2-{2-[3-(2-amino-ethylcarbomyl)-phenoxyl-1-azido-ethoxy}-ethoxy-acetic acid comprises one or more cleavage groups. In some embodiments, a rbNTP is attached to two spacer linkers (for example, separate linkers of a bifurcated linker construct), which may be the same or different, each of which terminates in a detection moiety. In some embodiments, two spacer linkers comprise a PEG and a 2-{2-[3-(2-amino-ethylcarbomyl)-phenoxyl-1-azido-ethoxy}-ethoxy-acetic acid linker, one or both of which may or may not comprise one or more cleavage groups, terminating in a detection moiety. In some embodiments, two spacer linkers may be two PEG linkers which may be of equal or unequal lengths (e.g., one PEG4 and the other PEG12), each of the PEG linkers terminating in a detection moiety, further with or without a cleavage group.

Examples of linkers can be found at, for example U.S. Pat. Nos. 7,816,503, 7,771,973, and patent application 2010/00317531 (each of which are incorporated herein by reference in their entireties). Methods and compositions as described herein are not limited by any particular spacer linker and alternatives will be readily apparent to a skilled artisan and are considered within the scope of the present disclosure.

In some embodiments, a spacer linker comprises one or more cleavage groups. Cleavage groups for use in methods as described herein may include, but are not limited to disulfide groups, acid labile groups, Sieber groups, indole groups, t-butyl Sieber groups, electrophilically cleavable groups, nucleophilically cleavable groups, photocleavable groups, cleavage groups that cleave under reductive conditions, oxidative conditions, cleavage via use of safety-catch groups, cleavage by elimination mechanism and metal assisted cleavable groups. As used herein, the term "cleavable linker" is considered equivalent to a spacer linker that comprises one or more cleavage groups. A discussion of linkers can be found at, for example, Guiller et al, 2000, Chem. Rev. 100:2091-2157 and as provided in U.S. Pat. No. 7,771,973, both of which are incorporated herein by reference in their entireties. Methods and compositions as described herein are not limited by any particular cleavage group and alternatives will be readily apparent to a skilled artisan and are considered within the scope of the present disclosure.

In some embodiments, reversibly blocked modified nucleotides as described herein are attached to a small molecule via a linker. In some embodiments, a linker comprises one or more cleavable groups and may be referred to as a cleavable linker. Cleavable groups include, but are not limited to, disulfide, diol, diazo, ester, sulfone azide, allyl and silyl ether, azide and alkoxy groups. In preferred embodiments, one or more of an azide, an alkoxy and a disulfide group is associated with reversibly blocked nucleotide (rbNTP) with another molecule, for example a hapten or a detection moiety, or both, for use in methods as described herein. Incorporation of a disulfide bond into a linker as described herein can be accomplished in a number of ways, for example as provided here, as found in U.S. Pat. No. 7,771,973, or as described in Hermanson, Bioconjugate Techniques, Second Edition, Academic Press (incorporated herein by reference in their entireties).

In some embodiments, a composition comprising a cleavage agent is added to a sequencing reaction to cleave a cleavage group in a spacer linker of a rbNTP conjugate. The cleavage agent added is dependent on the cleavage group present. For example, cleavage of disulfide bonds or other reductive cleavage groups is accomplished by a reducing agent. Reduction of a disulfide bond results in the release of the rbNTP from the linked molecule, for example a hapten, hapten conjugate and/or detection moiety such as a fluorescent moiety. Reducing agents useful in practicing embodiments as described herein include, but are not limited to, phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol and tris (2-carboxyethyl)phosphine (TCEP), tris(hydroxymethyl)phosphine (THP) and β-[tris(hydroxymethyl)phosphine] propionic acid (THPP). In some embodiments, a reducing agent used for cleaving a disulphide bond in a linker as described herein is DTT. In some embodiments, the concentration of a reducing reagent, for example DTT, utilized for cleaving a disulfide bond is at least 1 to 1000 mM, at least 20 to 800 mM, at least 40 to 500 mM, and preferably at least 50 to 200 mM. In some embodiments, a reducing agent used for cleaving a disulphide bond in a linker as described herein is a phosphine reagent, a water soluble phosphine reagent, a nitrogen containing phosphine reagent and salts and derivatives thereof. Exemplary phosphine reagents include, but are not limited to, TCEP, THP and those disclosed in US patent publication 2009/0325172 (incorporated herein by reference in its entirety) such as triaryl phosphines, trialkyl phosphines, sulfonate containing and carboxylate containing phosphines and derivatized water soluble phosphines. In some embodiments, the concentration of a phosphine utilized for cleaving a disulfide bond is at least 0.5-500 mM, at least 5 to 50 mM, and preferably at least 10 to 40 mM. Methods and compositions as described herein are not limited by any particular cleavage group and alternatives will be readily apparent to a skilled artisan and are considered within the scope of the present disclosure.

In some embodiments, a linker as described herein, which may or may not comprise a cleavage site, links a rbNTP to a fluorescent moiety and a fluorescence transition pattern for detecting incorporation of the nucleotide into a SBS reaction is realized by the addition of a quencher dye into a sequencing cycle. For example, a rbNTP conjugated to a fluorescent moiety via a linker (wherein the linker may or may not comprise a cleavage site) is added to a sequencing reaction. A first image is recorded thereby establishing a first detection pattern. During an intermediate reaction step, a quencher dye is added to the reaction (e.g., in lieu of a FRET partner removed from the reaction via a cleavage step) wherein the quencher dye sufficiently quenches the fluorescence of the aforementioned fluorescent moiety resulting in a detectable fluorescence change pattern (e.g., fluorescence to non or minimal fluorescence) upon a subsequent imaging step for that nucleotide. This embodiment is an alternative to a FRET donor/acceptor system as described herein, wherein the combination of two dyes results in fluorescence and the removal of one of the dyes, for example by a cleavage reaction, results in loss of fluorescence.

Quenching dyes as envisioned herein include, but are not limited to, those substances that absorb the excitation energy of a fluorophore, effectively quenching fluorescence of the target fluorophore, however are not typically fluorescent themselves. Examples of quencher dyes include, but are not limited to dark quenchers such as DABCYL (absorbs in the green spectrum), Iowa black FQ (absorbs in the green-yellow spectrum), Iowa black RQ (absorbs in the orange-red spectrum), IRDye QC-1 (absorbs in the 500-900 nm range) and Black Hole Quencher™ dyes (absorbs in the 500-700 nm range). For example, DABCYL is oftentimes used to quench fluorescein fluorescence and Black Hole Quencher™ dyes are utilized to quench fluorescence from FAM, TET, HEX, JOE, TAMRA, ROX and CY dyes depending on the characteristics (e.g., absorbance maximum) of the particular Black Hole Quencher™. In additional embodiments, such dark quenchers can be utilized in a FRET system, wherein the cleavage of the dark quencher during an intermediate step results in a fluorescence state change from quenched fluorescence to fluorescence, thereby establishing a detection pattern for incorporation of a nucleotide into a SBS reaction cycle.

Use of dye quenching embodiments as described herein are contemplated for use in permutations and combinations for detecting incorporation of a nucleotide into a SBS cycle as recognized by a skilled artisan. For example, a rbNTP may be linked to a fluorescent moiety wherein a quencher dye is utilized to determine nucleotide incorporation, a second rbNTP may be linked to a biotin wherein addition of a SA-fluorescent moiety is utilized to determine nucleotide incorporation and a third dye may be linked to a fluorescent moiety wherein a cleavage reaction is utilized to determine nucleotide incorporation. Methods as described herein are not limited by which nucleotide is conjugated to which particular detection system, other than their combination allows for the determination of incorporation of nucleotides into a sequencing reaction.

In some embodiments, the fluorescent detection moiety is modified to provide a detectable fluorescence difference between image 1 and image 2. For example, a fluorescent moiety which is attached either directly or indirectly to a rbNTP can be imaged during a first image event. Between the first and second image event a chemical, small molecule, etc. may be added to the sequencing reaction such that the structure of the fluorophore is modified thereby rendering the fluorescent moiety undetectable or minimally detectable during the second imaging event. For example, a cleavage agent which targets one or more bonds and/or structural entities of the fluorescent moiety may be added which may destroy the fluorescent nature of the fluorescent moiety thereby allowing for the detection of image states indicative of the incorporation of the attached rbNTP. As such, modifications of the fluorescent moiety itself can provide for detectable changes in imaging states which may be advantageous in methods as described herein.

In some embodiments of the present disclosure, a nucleotide type for use in a sequencing reaction is a rbNTP conjugate comprising a base, for example a natural or a modified base. In preferred embodiments, a base is a modified base. In preferred embodiments, a modified base comprises three phosphate groups off the sugar backbone, as such is a triphosphate, as denoted by NTP. In preferred embodiments, the modified base is reversibly blocked wherein the NTP comprises a reversible terminator 3' blocking group which, once removed, allows for continued extension in a sequence by synthesis sequencing reaction. In some embodiments, the 3' blocking group comprises an azido and/or alkoxy group and is removable by cleavage with a phosphine reagent. Such nucleotides are termed "reversibly blocked" or "rb", a type of which is a "fully functional" or "ff" NTP (commercially available at Illumina, Inc.). Further discussion of rbNTPs is found at, for example, U.S. Pat. Nos. 7,816,503 and 7,771,903 and United States patent application publication US2010/00317531 (each of which is incorporated herein by reference in its entirety)

Disclosed methods for nucleic acid detection find particular utility when used in sequencing, for example sequencing by synthesis (SBS) technologies. Sequencing by synthesis generally comprises sequential addition of one or more fluorescently labeled nucleotides to a growing polynucleotide chain in the 5' to 3' direction using a polymerase. The extended polynucleotide chain is complementary to the nucleic acid template affixed on the substrate (e.g., flowcell, chip, Slide, etc.), the target sequence. In some embodiments, the identity of an incorporated nucleotide in the extended chain is determined after two imaging steps thereby providing real time incorporation sequence data.

Disclosed method for nucleic acid detection also find utility when used in sequencing by ligation, sequencing by hybridization, and other sequencing technologies wherein "dark" nucleotide and/or orthogonal nucleotide modification schemes are employed.

Sequence by ligation is a sequencing method wherein a sequencing primer is elongated on a target sequence by ligating a probe comprising a nucleotide type (e.g., A, T, C or G), wherein the probe ligated is indicative of the sequence of the subsequent nucleotide in a target nucleotide string. Sequencing by ligation probes may comprise cleavage sites which can be cleaved following a ligation event so that another round probe addition, ligation, and nucleotide incorporation determination can be performed. An exemplary sequence by ligation methodology is di-base encoding (e.g., color space sequencing) utilized by Applied Biosystems' SOLiD™ sequencing system. Di-base encoding, or "color space" sequencing utilizes interrogation probes comprising 2 probe specific bases (e.g., made up of all possible combinations of the four different nucleotide types) followed by three degenerate bases and six universal bases, wherein each of the interrogation probes is linked to one of four different fluorescent dyes. The probes are added to a sequencing reaction comprising a target and a sequencing primer and a thermostable ligase ligates the di-base probe complementary to those sequences adjacent to the sequencing primer as found on the template. Fluorescence is detected by four color imaging, the ligated probes are cleaved to remove the fluorescent dye and regenerate the 5' phosphate for additional rounds of ligation and detection. Each template base is interrogated twice. Following several rounds of ligation and detection of one sequencing primer, the synthetic strand is denatured, a new sequencing primer is added, and the process of ligation detection begins anew. The di-coded fluorescent color space data bits are aligned, applied to a color space reference genome grid and sequence is determined (Voelkerding et al., 2009, Clin Chem 55:641-658; incorporated herein by reference in its entirety).

The modified nucleotides disclosed herein could be utilized in sequence by ligation technologies. For example, probes from a two base encoding scheme in which four dinucleotide sequences are associated with one color, for example AA, CC, GG and TT may be associated with a blue fluorescent dye, another four dinucleotide sequences are associated with a red dye, another four a green dye are detection is via a four color imaging system could be modified as described herein. The incorporation of less than four dyes, for example one dye or two or more dyes of similar excitation/emission while practicing chemical and/or enzymatic manipulations would allow for fewer imaging events thus more simplified instrument optics. For example, a probe comprising four dinucleotide sequences such as AA, CC, GG and TT, further comprising a number or degenerate and/or universal nucleotides (optionally), could further comprise a linker containing a cleavage site (for example an azide or alkoxy cleavage site) linking the dinucleotide with a fluorescent moiety. A probe comprising a second set of four dinucleotides, for example TA, GC, CG and AT, further comprising a number or degenerate and/or universal nucleotides (optionally), could further comprise a linker containing two cleavage sites (the second cleavage site different from the first, for example a SS linkage) linking the dinucleotide with a fluorescent moiety. A probe set comprising a third set of four dinucleotides, for example CA, AC, GT and TG, further comprising a number or degenerate and/or universal nucleotides (optionally), could further comprise a linker containing a cleavage site linking the dinucleotide with a hapten moiety (for example biotin). The fourth probe set of four dinucleotides could comprise additional nucleotides, linkers, etc. however would lack a fluorescent moiety. The probes could be added to the sequencing by ligation reaction, ligated to the template and a first image could be recorded to capture a first signal state. A cleavage reagent could be added to the reaction to cleave the second cleavage site (e.g., SS linkage) thereby releasing the fluorescent moiety, a hapten binding partner (for example streptavidin) conjugated to a fluorescent moiety could be added and a second image could be recorded to capture a second signal state. A cleavage agent to the first cleavage site (e.g., azide/alkoxy) could be added to the reaction to release all the fluorescent moieties and the next round of sequencing by ligation could be carried out. Signal states could be aligned and sequences determined.

Sequence by hybridization comprises the use of an array of short sequences of nucleotide probes to which is added fragmented, labeled target DNA (Drmanac et al., 2002, Adv Biochem Eng Biotechnol 77:75-101; Lizardi et al., 2008, Nat Biotech 26:649-650; incorporated herein by reference in their entirety). The fragments hybridize to their complementary probe on the array and the hybridization is captured by the attached label such as a fluorescent dye thereby determining the sequence of the target. Some applications of sequence by hybridization utilize probes that comprise universal (e.g., nucleotide analogs) and designated nucleotides and are referred to as gapped probes, the use of which is reported to increase the sensitivity of hybridization and thereby detection of the sequencing assay (U.S. Pat. No. 7,071,324, incorporated herein by reference in its entirety). Further improvements to sequence by hybridization can be found at, for example, US patent application publications 2007/0178516, 2010/0063264 and 2006/0287833 (incorporated herein by reference in their entireties). However, regardless of the method oftentimes complex optics systems are needed to capture hybridization events.

The modified nucleotides disclosed herein could be utilized in sequence by hybridization technologies. Nucleic acid probes from multiple different samples for sequence determination which are hybridized to arrayed probes could be modified to comprise attributes disclosed herein for use in minimal dye sequencing thereby allowing for less complex optics with concurrent sequence determination of multiple different test samples. For example, a test sample probe (e.g., fragmented test nucleic acids) could be modified to comprise a linker containing a cleavage site (for example an azide or alkoxy cleavage site) linking the probe with a fluorescent moiety. A second probe set could be modified to comprise a linker containing two cleavage sites (the second cleavage site different from the first, for example a SS linkage) linking the second probe with a fluorescent moiety. A third probe set could comprise a linker containing a cleavage site linking the nucleic acid probe with a hapten moiety (for example biotin). The probes could be added to a sequence by hybridization type of array, hybridization reactions of the modified test probes to the immobilized probes on the array carried out, and a first image recorded to capture a first signal state. A cleavage reagent could be added to the reaction to cleave the second cleavage site (e.g., SS linkage) thereby releasing the fluorescent moiety, a hapten binding partner (for example streptavidin) conjugated to a fluorescent moiety could be added and a second image recorded to capture the second signal state. Signal states could be determined, wherein the two image signal state grid could be used to determine the location and thereby the sequence of the multiple different hybridized test probes.

Sequencing approaches which combine hybridization and ligation biochemistries have been developed and commercialized, such as the genomic sequencing technology practiced by Complete Genomics, Mountain View, CA). For example, combinatorial probe-anchor ligation, or cPAL™ (Drmanac et al., 2010, Science 327(5961): 78-81) utilizes ligation biochemistry while exploiting advantages of sequence by hybridization. Briefly, sequencing of the target DNA nanoballs comprises detecting ligation products that are formed by an anchor oligonucleotide that is hybridized to an adaptor sequence which is subsequently ligated to a fluorescently labeled degenerate sequencing probe comprising one of four specified nucleotides at the interrogation position. Ligation occurs when the nucleotide at the interrogation position is complementary to the nucleotide at the detection site within the target DNA nanoball. The resulting stable probe/anchor ligation product is fluorescently detected. After the read, the entire anchor/probe complex is released, the next anchor is hybridized to the DNA target, and the process is repeated. As with many sequencing reactions, four differently detectable dyes are utilized, one for each specified interrogation nucleotide A, C, G and T utilizing multiple detection optics.

The modified nucleotides disclosed herein could be utilized in combinatorial probe-anchor ligation sequencing technologies. The incorporation of less than four dyes, would allow for fewer imaging events. For example, a probe comprising a number or degenerate nucleotides could further comprise a linker containing a cleavage site (for example an azide or alkoxy cleavage site) linking the interrogation nucleotide with a fluorescent moiety. A probe comprising a second set of degenerate nucleotides could further comprise a linker containing two cleavage sites linking the interrogation nucleotide with a fluorescent moiety. A probe set comprising a third set of degenerate nucleotides could further comprise a linker containing a cleavage site linking the interrogation nucleotide with a hapten moiety (for example biotin). The fourth probe set of degenerate nucleotides could comprise additional nucleotides, linkers, etc., however would lack a fluorescent moiety. The probes could be added to the cPAL™ reaction, ligated to the anchor/adaptor and a first image could be recorded to capture a first signal state. A cleavage reagent could be added to the reaction to cleave the second cleavage site (e.g., SS linkage) thereby releasing the fluorescent moiety, a hapten binding partner (for example streptavidin) conjugated to a fluorescent moiety could be added and a second image could be recorded to capture a second signal state. A cleavage agent to the first cleavage site (e.g., azide/alkoxy) could be added to the reaction to release all the fluorescent moieties and the next round of cPAL™ could be carried out. Signal states could be aligned and sequences determined.

Nucleic acids or polynucleotides for sequencing include, but are not limited to, nucleic acids such as DNA, RNA or PNA (peptide nucleic acid), variants or fragments thereof and/or concatamers thereof. The polynucleotides may be of known or unknown sequence, either naturally occurring or artificial in nature and can be of any source (e.g., eukaryotic or prokaryotic). The polynucleotides may be naturally derived, recombinantly produced or chemically synthesized. Concatamerized polynucleotides may contain subunits or analogs thereof that may or may not occur in nature, or modified subunits. Methods as described herein can be used to determine a sequence of a polynucleotide. The length of the target nucleic acid for sequencing may vary. For example, the nucleic acid for sequencing may include at least 10, at least 20, at least 30, at least 40, at least 50, at least 100, at least 200, at least 500, at least 1,000, at least 10,000, at least 100,000, at least 1,000,000, at least 10,000,000 nucleotides. The polynucleotide for sequencing may be genomic in origin or fragments or variants thereof. The nucleic acid strand for sequencing may be single stranded and may or may not be derived from a double-stranded nucleic acid molecule. Single stranded molecules may also be produced by, for example, chemical or in vitro synthesis methods and technologies. Embodiments as described herein are not limited by the nucleic acid preparatory methods and any number methods may be practiced by a skilled artisan in order to provide a composition for use in disclosed methods. For example, in sequence by synthesis methodologies oftentimes a library comprising the target nucleic acids is generated, and a portion of the DNA library is then sequenced.

Isolated DNA from samples, for example genomic DNA containing samples, is typically modified prior to characterization, for example by sequencing utilizing methods as described herein. Genomic DNA libraries are created which can be sequenced by practicing the methods as described herein. A library is produced, for example, by performing the methods as described in the Nextera™ DNA Sample Prep Kit (Epicentre® Biotechnologies, Madison WI), SOLiD™ Library Preparation Kits (Applied Biosystems™ Life Technologies, Carlsbad CA), and the like. A DNA library sample may be further amplified for sequencing by, for example, multiple stand displacement amplification (MDA) techniques.

For sequencing after MDA, an amplified sample library is, for example, prepared by creating a DNA library as described in Mate Pair Library Prep kit, Genomic DNA Sample Prep kits or TruSeq™ Sample Preparation and Exome Enrichment kits (Illumina®, Inc., San Diego CA).

DNA libraries can be immobilized on a flowcell and bridge amplification performed on the immobilized polynucleotides prior to sequencing, for example sequence by synthesis methodologies. In bridge amplification, an immobilized polynucleotide (e.g., from a DNA library) is hybridized to an immobilized oligonucleotide primer. The 3' end of the immobilized polynucleotide molecule provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension. Thus, the first and second portions can be amplified to produce a plurality of clusters. Clusters and colonies are used interchangeably and refer to a plurality of copies of a nucleic acid sequence and/or complements thereof attached to a surface. Typically, the cluster comprises a plurality of copies of a nucleic acid sequence and/or complements thereof, attached via their 5' termini to the surface. Exemplary bridge amplification and clustering methodology are described, for example, in PCT Patent Publ. Nos. WO00/18957 and WO98/44151, U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2005/0100900, U.S. Patent Publ. No. 2004/0002090; U.S. Patent Publ. No. 2007/0128624; and U.S. Patent Publ. No. 2008/0009420, each of which is incorporated herein by reference in its entirety. The compositions and methods as described herein are particularly useful in sequence by synthesis methodologies utilizing a flowcell comprising clusters.

Emulsion PCR methods for amplifying nucleic acids prior to sequencing can also be used in combination with methods and compositions as described herein. Emulsion PCR comprises PCR amplification of an adaptor flanked shotgun DNA library in a water-in-oil emulsion. The PCR is multi-template PCR; only a single primer pair is used. One of the PCR primers is tethered to the surface (5' attached) of microscale beads. A low template concentration results in most bead-containing emulsion microvesicles having zero or one template molecule present. In productive emulsion microvesicles (an emulsion microvesicle where both a bead and template molecule are present), PCR amplicons can be captured to the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods are set for in Dressman et al., Proc. Natl. Acad. Sci. USA 100:8817-8822 (2003), PCT Patent Publ. No. WO 05/010145, U.S. Patent Publ. Nos. 2005/0130173, 2005/0064460, and US2005/0042648, each of which is incorporated herein by reference in its entirety.

DNA nanoballs can also be used in combination with methods and compositions as described herein. Methods for creating and utilizing DNA nanoballs for genomic sequencing can be found at, for example, US patents and publications U.S. Pat. No. 7,910,354, 2009/0264299, 2009/0011943, 2009/0005252, 2009/0155781, 2009/0118488 and as described in Drmanac et al., 2010, Science 327(5961):78-81; all of which are incorporated herein by reference in their entireties. Briefly, following genomic DNA fragmentation consecutive rounds of adaptor ligation, amplification and digestion results in head to tail concatamers of multiple copies of the circular genomic DNA template/adaptor sequences which are circularized into single stranded DNA by ligation with a circle ligase and rolling circle amplified (as described in Lizardi et al., Nat. Genet. 19:225-232 (1998) and US 2007/0099208 A1, each of which is incorporated herein by reference in its entirety). The adaptor structure of the concatamers promotes coiling of the single stranded DNA thereby creating compact DNA nanoballs. The DNA nanoballs can be captured on substrates, preferably to create an ordered or patterned array such that distance between each nanoball is maintained thereby allowing sequencing of the separate DNA nanoballs.

A skilled artisan will recognize additional methods and technologies for amplifying nucleic acids which could also be used in combination with the methods and compositions described herein. Embodiments described herein are not limited to any DNA amplification method.

Methods as described herein are not limited by any particular sequencing sample preparation method and alternatives will be readily apparent to a skilled artisan and are considered within the scope of the present disclosure. However, particular utility is found when applying the methods herein to sequencing devices such as flow cells or arrays for practicing sequence by synthesis methodologies or other related sequencing technologies such as those practiced by one or more of polony sequencing technology (Dover Systems), sequencing by hybridization fluorescent platforms (Complete Genomics), sTOP technology (Industrial Technology Research Institute) and sequencing by synthesis (Illumina, Life Technologies).

In some embodiments, the methods set forth herein can be used in a modified version of manufacturer's protocols on a system such as those provided by Illumina®, Inc. (HiSeq 1000, HiSeq 2000, Genome Analyzers, MiSeq, HiScan, iScan, BeadExpress systems), Applied Biosystems™ Life Technologies (ABI PRISM® Sequence detection systems, SOLiD™ System), or other fluorescence based sequencing instrument, further as those described in, for example, United States patents and patent applications U.S. Pat. Nos. 5,888,737, 6,175,002, 5,695,934, 6,140,489, 5,863,722, 2007/007991, 2009/0247414, 2010/0111768 and PCT application WO2007/123744, and U.S. patent application Ser. Nos. 61/431,425, 61/431,440, 61/431,439, 61/431,429, 61/438,486 each of which is incorporated herein by reference in its entirety. Modifications to the commercial methods can include, but are not limited to, alteration of the labels used and addition of steps to change label states as set forth herein.

Output from a sequencing instrument can be of any sort. For example, current technology typically utilizes a light generating readable output, such as fluorescence or luminescence, however the present methods are not limited to the type of readable output as long as differences in output signal for a particular sequence of interest is potentially determinable. Examples of analysis software that may be used to characterize output derived from practicing methods as described herein include, but are not limited to, Pipeline, CASAVA and GenomeStudio data analysis software (Illumina®, Inc.), SOLiD™, DNASTAR® SeqMan® NGen® and Partek® Genomics Suite™ data analysis software (Life Technologies), Feature Extraction and Agilent Genomics Workbench data analysis software (Agilent Technologies), Genotyping Console™, Chromosome Analysis Suite data analysis software (Affymetrix®).

A skilled artisan will know of additional numerous commercially and academically available software alternatives for data analysis for sequencing generated output. Embodiments described herein are not limited to any data analysis method.

EXAMPLES

The following examples are provided in order to demonstrate and further illustrate certain embodiments and aspects of the present disclosure and are not to be construed as limiting the scope thereof.

Example 1—Synthesis of rbATP-LN3-DEG527-PEG4-Biotin

A branched biotinylated and fluorescently labeled, reversibly blocked adenine construct for use in SBS was synthesized as follows:

Lys-DEG527

To a solution of DEG527 (11 mg, 14.6 µmol) in dry DMA (2 ml) was added TSTU (5.3 mg, 17.5 µmol) and diisopropylethylamine (6.3 µl, 36.5 µmol). The mixture was stirred for 30 minutes at room temperature to full activation of the acid. A solution of Boc-lysine (18 mg, 73 µmol) in TEAB 0.1M (0.2 ml) was added to the reaction mixture. The mixture was stirred for 3 hours until TCL showed complete consumption of activated ester. The volatiles were evaporated under reduced pressure and the residue was dissolved in trifluoroacetic acid (0.1 ml), DCM (0.9 ml) and MeOH (0.1 ml). The solution was stirred at room temperature for 1 hour until TLC showed full consumption of the starting material. The solution was concentrated down to dryness, re-dissolved in TEAB 0.1 M (5 ml) and purified by RP-HPLC.

Lys-DEG527-PEG4-Biotin

To a solution of Lys-DEG527 (14 µmol) and diisopropylethylamine (15 µl, 84 µmol) in dry DMA (5 ml), was added PEG4-biotin-NHS (41 mg, 70 µmol). The mixture was sonicated for several minutes and then continuously stirred for several hours. TCL showed complete consumption of lys-DEG527. The volatiles were evaporated under reduced pressure. The residue was re-dissolved in TEAB 0.1 M (5 ml) and purified by RP-HPLC.

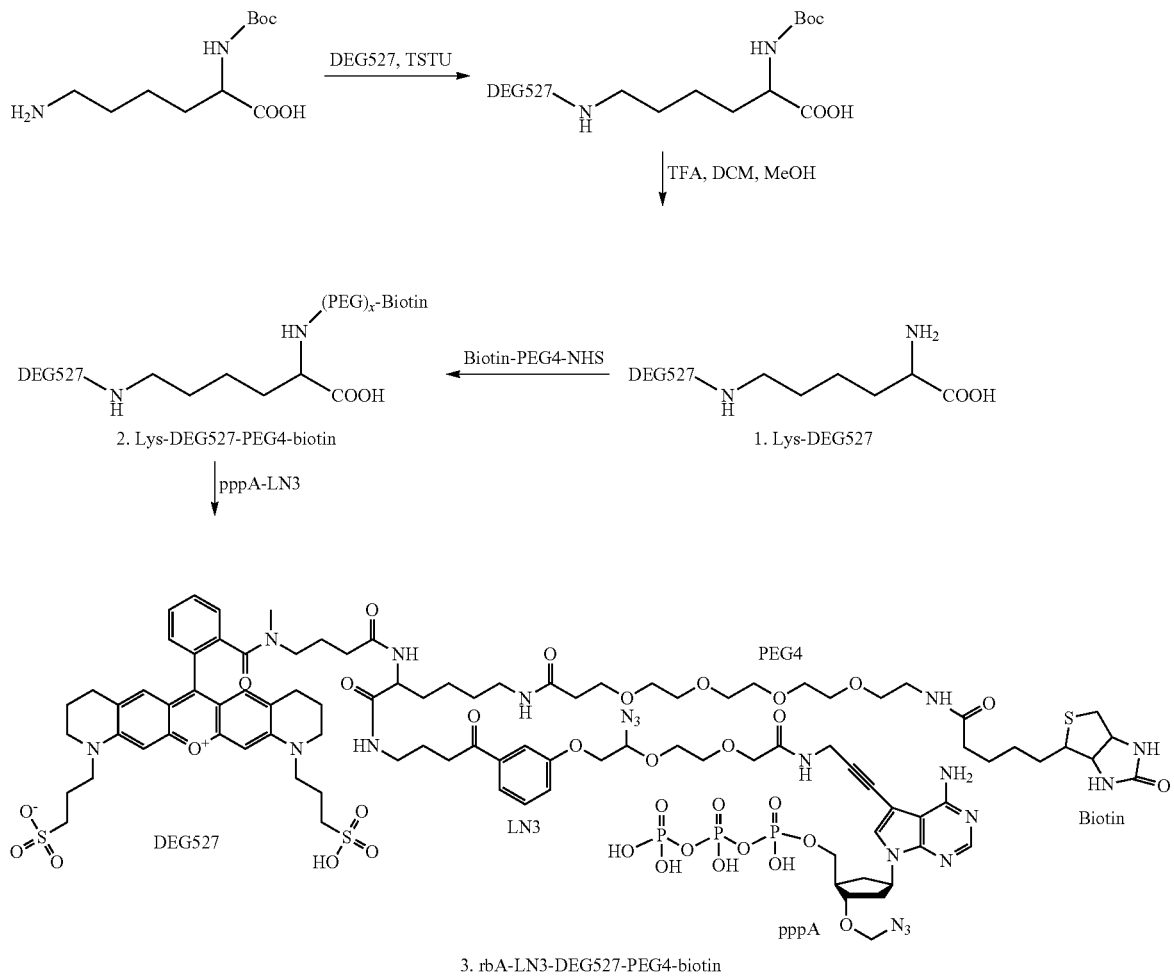

3. rbA-LN3-DEG527-PEG4-biotin rbATP-LN3-DEG527-PEG4-Biotin

To a solution of Lys-DEG527-PEG4-biotin (9 µmol) in dry DMA (2 ml), was added TSTU (3.3 mg, 10.8 µmol) and diisopropylethylamine (4 µl, 22.5 µmol). The mixture was stirred for 30 minutes at room temperature to full activation of the acid. A solution of LN3-pppA (18 µmol) in TEAB 0.1M (0.2 ml) was added to the reaction mixture. The mixture was stirred for 5 hours until TCL showed complete consumption of activated ester. The reaction was quenched with TEAB buffer (0.1M, 10 ml) and loaded on a DEAE Sephadex column (2×5 cm). The column was eluted with a gradient of 0.1M to 1M TEAB buffer in 30 min at 25 ml/min. The fractions containing the product were combined, evaporated and purified by HPLC.

Example 2—Synthesis of rbCTP-LN3-PEG4-Biotin

A biotinylated, reversibly blocked cytosine construct for use in SBS was synthesized as follows:

rbCTP-LN3-PEG4-Biotin

To a solution of PEG4-biotin-NHS (17.7 mg, 30 µmol) and diisopropylethylamine (8.7 µl, 50 µmol) in dry DMA (3 ml), was added a solution of LN3-pppC (10 µmol) in TEAB 0.1M (0.3 ml). The mixture was stirred at room temperature for 5 hours. The reaction progress was monitored by RP-HPLC until complete consumption of LN3-pppC. The reaction was quenched with TEAB buffer (0.1M, 10 ml) and loaded on a DEAE Sephadex column (2×5 cm). The column was eluted with a gradient of 0.1M to 1M TEAB buffer in 30 min at 25 ml/min. The fractions containing the product were combined, evaporated and purified by HPLC.

Example 3—Synthesis of rbATP-LN3-SS-DEG527

A fluorescently labeled, fully functional adenine construct comprising a cleavable linker for use in SBS was synthesized as follows:

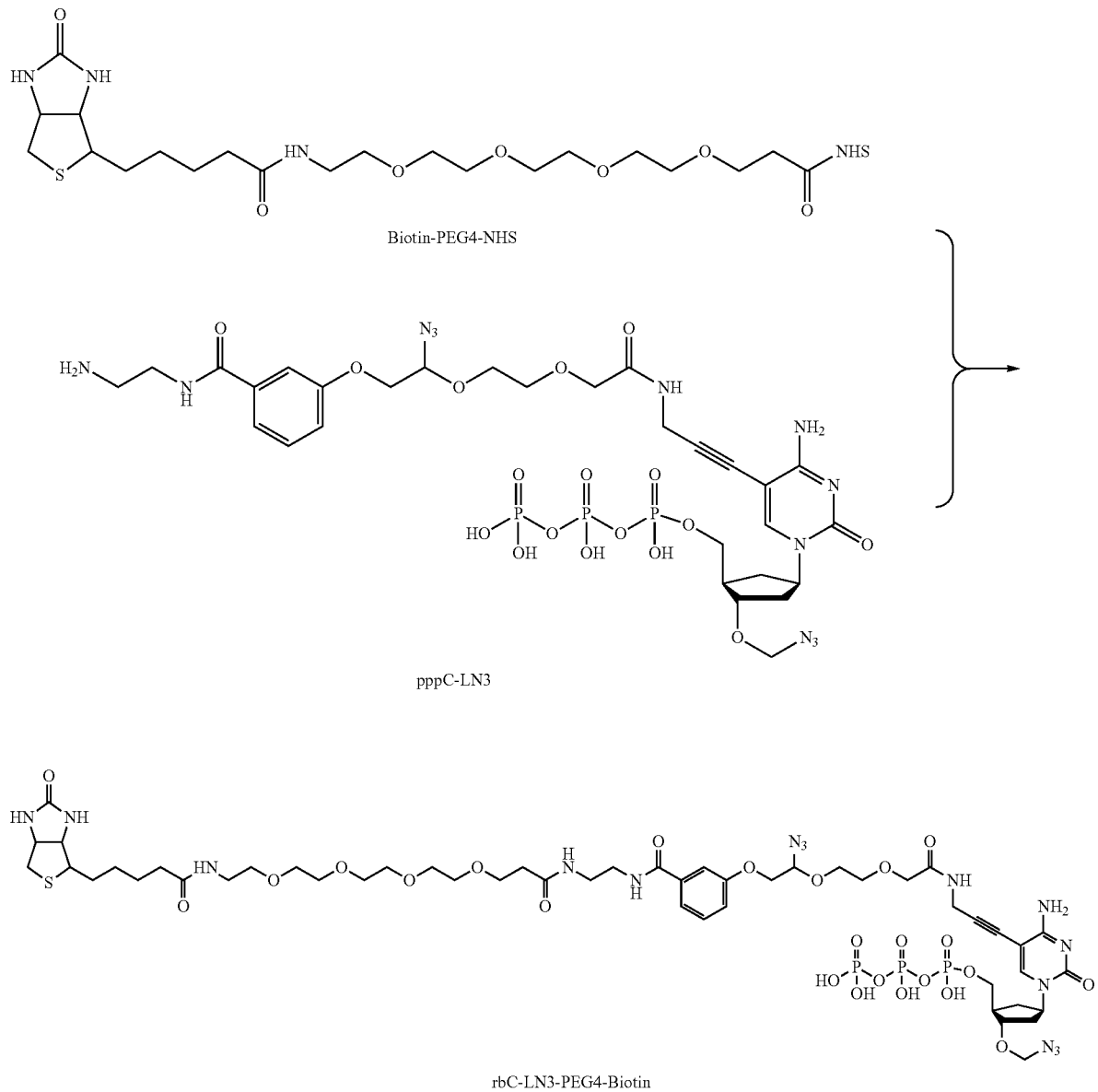

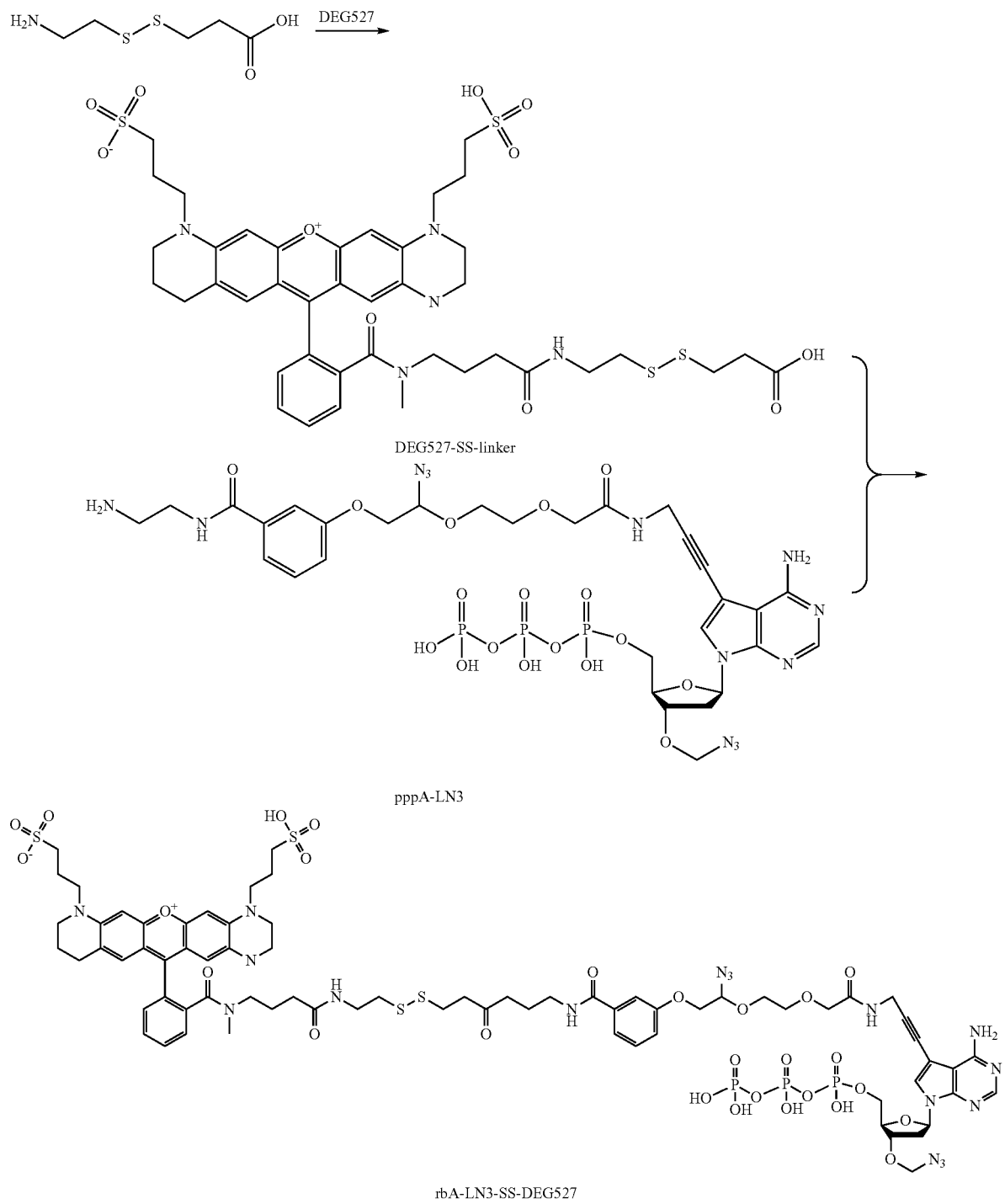

DEG527-SS-Linker

To a solution of DEG527 (12.5 mg, 16 μmol) in dry DMA (2 ml), was added TSTU (6 mg, 20 μmol) and diisopropylethylamine (7 μl, 40 μmol). The mixture was stirred for 30 minutes room temperature to full activation of the acid. A solution of SS-linker (9 mg, 50 μmol) in TEAB 0.1M (0.2 ml) was added to the reaction mixture. The mixture was stirred for 3 hours until TCL showed complete consumption of activated ester. The volatiles were evaporated under reduced pressure and the residue was dissolved in TEAB 0.1M (5 ml) and purified by RP-HPLC.

rbATP-LN3-SS-DEG527

To a solution of DEG527-SS-linker (5.9 μmol) in dry DMA (2 ml), was added TSTU (2.1 mg, 7.1 μmol) and diisopropylethylamine (2.6 μl, 14.8 μmol). The mixture was stirred for 30 minutes at room temperature to full activation of the acid. A solution of LN3-pppA (17.7 μmol) in TEAB 0.1M (0.2 ml) was added to the reaction mixture. The mixture was stirred for 5 hours until TCL showed complete consumption of activated ester. The reaction was quenched with TEAB buffer (0.1M, 10 ml) and loaded on a DEAE Sephadex column (2×5 cm). The column was eluted with a gradient of 0.1M to 1M TEAB buffer in 30 min at 25 ml/min. The fractions containing the product were combined, evaporated and purified by HPLC.

Example 4—Detection of Nucleotide Incorporation Using Biotin Conjugated Nucleotide Construct Experiments were performed to demonstrate the use of a biotin conjugated nucleotide in sequencing reactions. The time space signature of the experiments followed the time space imaging pattern

|   | Image 1 | Image 2 |
|---|---|---|
| A | 1 | 0 |
| C | 0 | 1 |
| G | 0 | 0 |
| T | 1 | 1 |

Experiments were performed on a Genome Analyzer IIx configured in single-lane mode. A standard sequence by synthesis enzymology incorporation program was followed using the reversibly blocked nucleotide mix including an unlabelled rbGTP, fluorescently labeled rbTTP-LN3-NR550, biotinylated rbCTP-LN3-PEG4-biotin and rbATP with a cleavable disulfide (SS) linker rbATP-LN3-SS-DEG527. Data acquisition and analysis differed from the standard 4-dye SBS chemistry. Briefly, after a nucleotide incorporation step, the clusters were laser excited and a fluorescent image was acquired. Additional reaction components were added to the reaction to selectively cleave the SS bond of rbATP-LN3-SS-DEG527 and SA-NR555 was added to selectively label rbCTP-LN3-biotin to create rbCTP-LN3-biotin-SA-NR555. The clusters were laser excited a second time a second fluorescent image was recorded. So, incorporation of each of the four bases is by changes, or lack thereof, of fluorescent intensity states using dyes that excite and emit in the same wavelength.

A genomic DNA library was created for use in single read sequencing on a Genome Analyzer IIx (Illumina, Inc.). Following library preparation, a sequencing flowcell with target sequencing clusters was creating using the TruSeq SR Cluster Kit v2 on the Illumina® cBot following manufacturer's protocol for single read sequencing. Following cluster generation, the flowcell was placed in a Genome Analyzer IIx and the sample was sequenced using reagents from TruSeq SBS Reagent Kit v5 (Illumina®, Inc.).

Stock solutions of the reversibly blocked nucleotides for use in the sequencing reaction were prepared; 100 µM stock solutions of dark or unlabelled rbGTP, rbATP-LN3-SS-DEG527, rbCTP-PEG4-biotin and rbTTP-LN3-NR550. A stock solution of streptavidin-NR555 (SA-NR555 at 1 mg/ml) was prepared in a Binding and Wash buffer (5 mM Tris pH 7.5, 0.5 mM EDTA, 1M NaCl).

For the Genome Analyzer IIx, the instrument reagent positions were re-configured for single dye sequence by synthesis. One lane was selected for sequencing and the other lanes were disconnected thereby ensuring that reagents were drawn through one sequencing lane and that no crossover of any liquid from another lane could occur. Reagents were placed on the Genome Analyzer IIx (GAIIx) as follows:

| Position | Reagent |
|---|---|
| 1 | Incorporation Mix (IMX) |
| 2 | Blank |
| 3 | Scan Mix (SMX) |
| 4 | Blank |
| 5 | Incorporation Buffer (PR2) |
| 6 | Cleavage Mix (CLM) |
| 7 | Blank |
| 8 | SA-NR555 |

Reagents were prepared for a 150 cycle sequencing assay. From the TruSeq SBS Reagent Kit v5, reagents CLM, SMX and PR2 were utilized as instructed. For the IMX reagent containing the reversibly blocked nucleotides, to 20.1 ml of IMX buffer was added 1 ml of rbATP-SS-DEG527 (final concentration 4 µM), 0.5 ml rbGTP (final concentration 2 µM), 2.5 ml rbCTP-PEG4-biotin (final concentration 10 µM) and 0.25 ml rbTTP-LN3-NR550 (final concentration 1 µM). The rbNTP solution was filtered and 0.6 ml of High Density polymerase (HDP, final concentration 15 µg/ml) was added. A 1:200 dilution of SA-NR555 was made in Binding and Wash buffer.

Reagents were loaded on the Genome Analyzer IIx and sequencing protocol was run. Briefly, a standard incorporation step (i.e., FirstBase) was followed by imaging as described in the manufacturer's protocol. The imaging was immediately followed by disulphide cleavage (addition of CLM) and SA-NR555 (addition of 1:200 dilution SA-NR555) binding and a subsequent second imaging followed by a standard de-block and incorporation step (i.e., CompleteCycle). Cleavage of the disulphide bonds resulting in a change in intensity state for rbATP from 1 to 0 was selective and proceeded at a rapid rate of <5 seconds at room temperature. Biotin/streptavidin binding also occurring rapidly at a rate of <25 seconds at room temperature resulting in a change in intensity state for rbCTP from 0 to 1.

Total cycle time excluding imaging was around 9.3 minutes. Cycling was repeated for the remaining cycles. The general flow is illustrated in FIG. 11.

Figure 2:
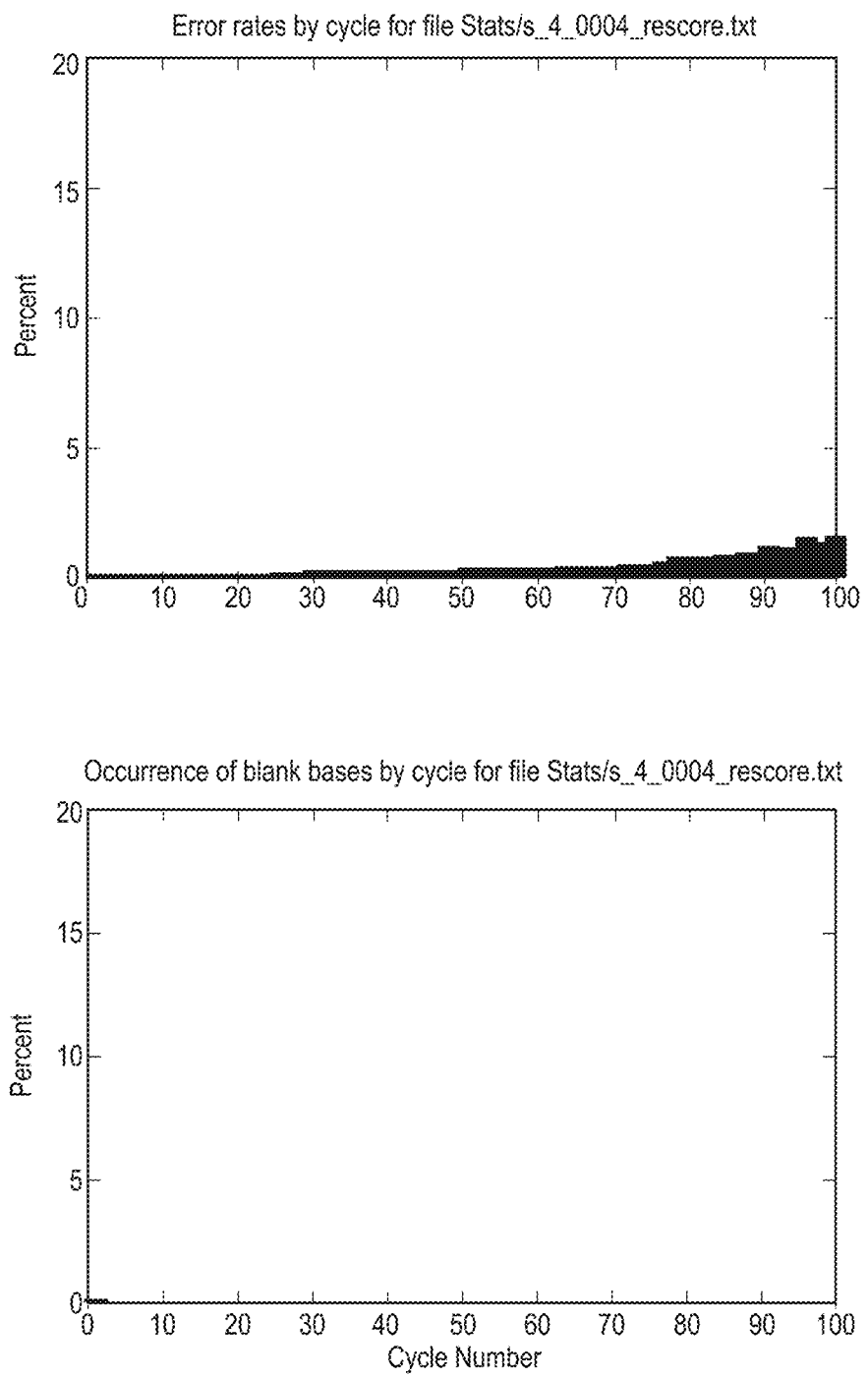
FIG. 2 shows exemplary graphs reporting percentage (Y axis) error rates (top) and blank base calls (bottom) in a sequencing reaction on a cycle by cycle basis (X axis).

Exemplary results can be found in FIGS. 1 and 2 and Table 1. FIG. 1 exemplifies a cloud style heat map recorded at different cycles throughout the sequencing run. The cloud maps demonstrate that differentiation of the four nucleotides was successful (the bottom isolated and nucleotide labeled cloud map orients the positions of the four nucleotides within the cloud map). FIG. 2 reports an exemplary tracking of error rate percentages of nucleotide incorporation over a 100 cycle sequencing run for the selected lane 4, tile 4. An error rate of 0.0.4% over 100 cycles for lane 4, tile 4 on a flowcell was recorded, whereas FIG. 2 demonstrates that there were no blank base calls throughout the 100 cycle run for that lane and tile. Phasing was reported at 0.27% and prephasing at 0.43%. Table 1 shows results from lane 4, tiles 1-6.

Table 1

| Lane | Tile | Clusters (raw) | % PF Clusters | % Align (PF) | Av Alignment Score (PF) | % Error Rate (PF) |
|---|---|---|---|---|---|---|
| 4 | 1 | 288360 | 77.64 | 96.08 | 121.87 | 0.51 |
| 4 | 2 | 285563 | 78.67 | 96.04 | 121.39 | 0.7 |
| 4 | 3 | 282653 | 79.5 | 96.12 | 121.97 | 0.48 |

-continued

| Lane | Tile | Clusters (raw) | % PF Clusters | % Align (PF) | Av Alignment Score (PF) | % Error Rate (PF) |
|---|---|---|---|---|---|---|
| 4 | 4 | 280818 | 79.07 | 95.92 | 121.87 | 0.4 |
| 4 | 5 | 283422 | 78.36 | 96.05 | 121.97 | 0.43 |
| 4 | 6 | 282958 | 61.68 | 60.7 | 74.58 | 2.22 |

Example 5—Detection of Nucleotide Incorporation Using One Dye

Experiments were performed to demonstrate that one dye can be used to determine the sequence of a nucleic acid.

The nucleotides utilized in this experiment included:

rbATP-LN3-SS-NR550C4 rbTTP-LN3-NR550C4 rbCTP-(LN3)$^2$-Biotin rbGTP-no label

Figure 5:
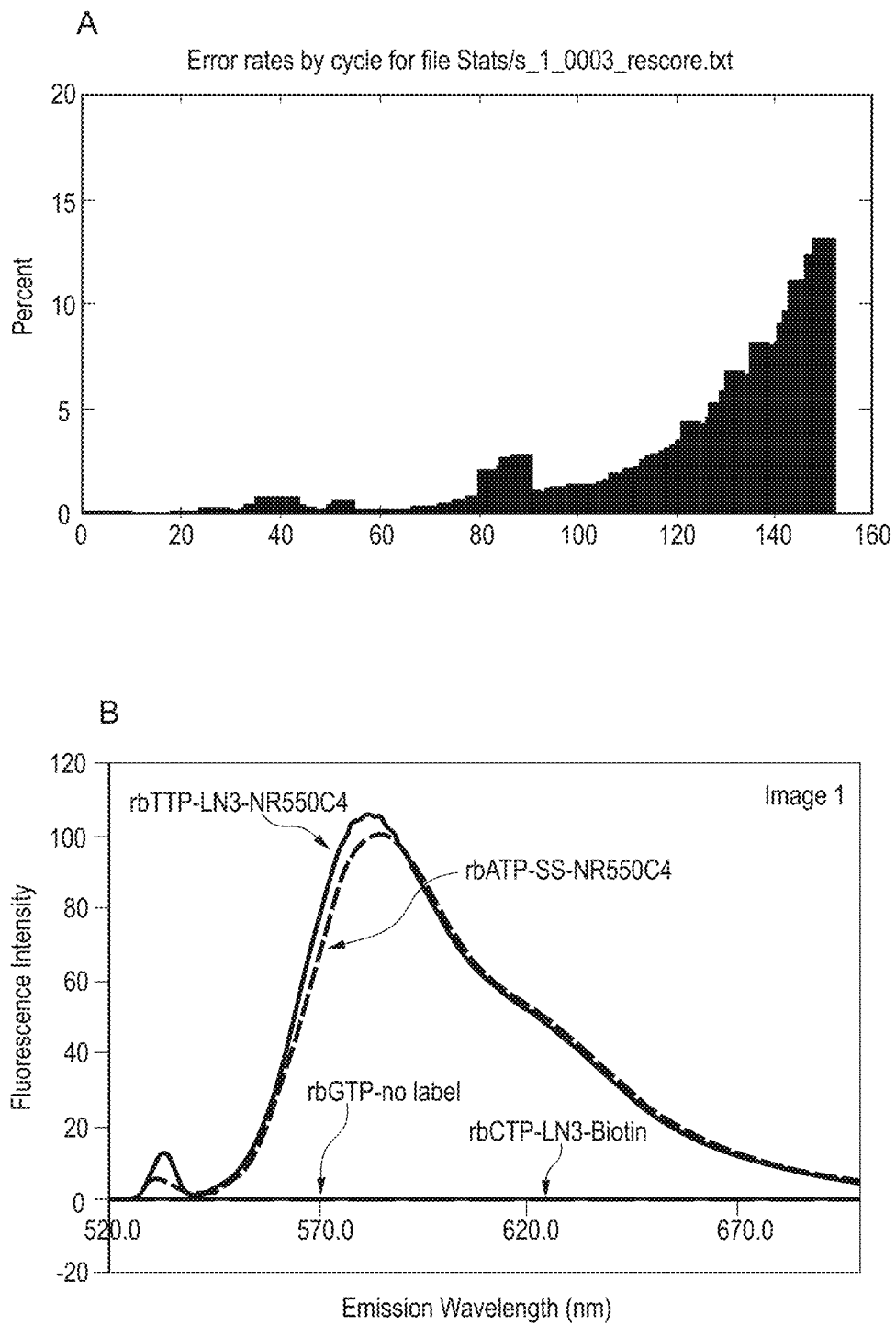
FIG. 5 shows A) the error rate of basecalls for an experiment using one dye in a sequencing reaction, B) exemplary fluorescent patterns for each of the modified nucleotides in a first image event (Image 1) using only one dye, C) exemplary fluorescent patterns for each of the modified nucleotides in a second image event (Image 2)
Figure 5:
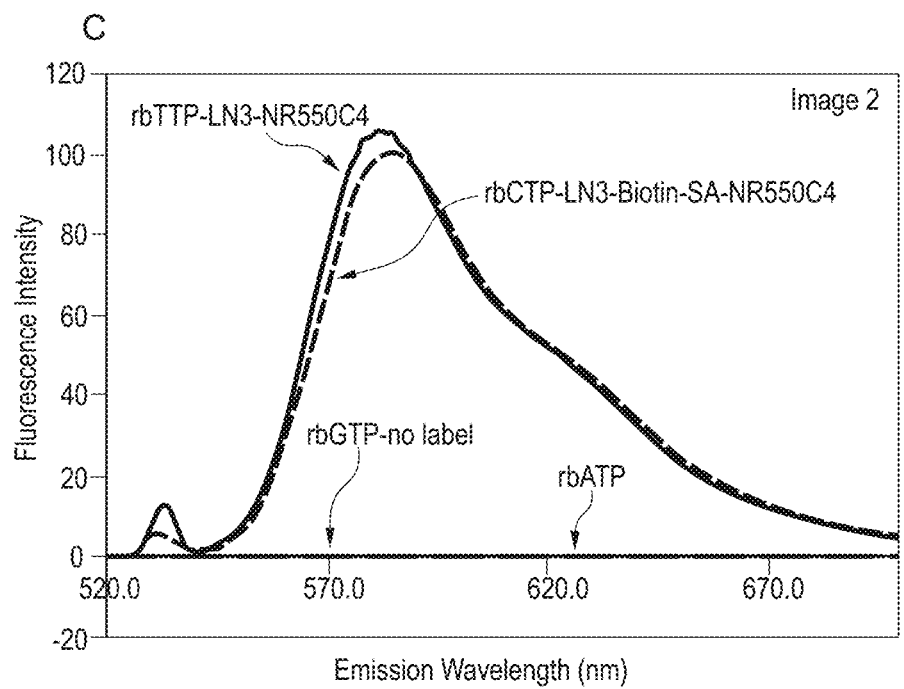
Figure 5:
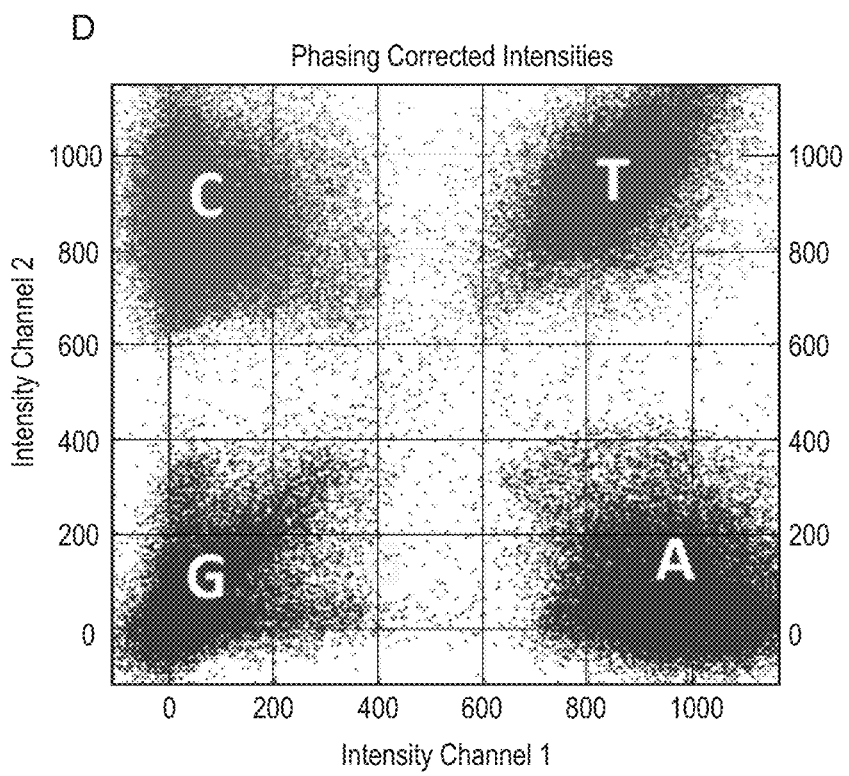

All nucleotide stock concentrations were stored at 100 µM in 10 mM Tris Buffer (pH 8.0). The fluorescent moiety used to label the nucleotides was NR550C4. Two representative emission spectra for the dye on rbATP and rbTTP are shown in FIG. 5B. The rbGTP was not labeled and therefore was considered the "dark" nucleotide. For determining the incorporation of cytosines into a growing nucleic acid strand, a master mix which included a conjugate of streptavidin-NR550C4 was added to the reaction as detailed below.

Synthesis of the NR550C4-SS-linker composition was performed as previously described for DEG527-SS-linker composition, except the NR550C4 fluorescent moiety was used in lieu of the DEG527 fluorophore. Synthesis of the rbATP-LN3-SS-NR550C4 composition was performed as previously described for rbATP-LN3-SS-DEG527, however the NR550C4-SS-linker composition was used in lieu of the DEG527-SS-linker composition. Synthesis of the rbTTP-LN3-NR550C4 composition was performed as described for rbATP-LN3-SS-550C4, however rbTTP-LN3 was used in lieu of rbATP-LN3 and NR550C4 was used in lieu of NR550C4-SS-linker. Synthesis of the rbCTP-(LN3)$^2$-Biotin was performed as previously described for rbCTP-LN3-PEG4-Biotin, except that LN3-Biotin was used instead of biotin during the amide coupling reaction.

Streptavidin was conjugated to NR550C4 by methods known in the art, and a stock solution of Strep-NR550C4 (SA-NR550C4) at 1 mg/ml was prepared in a buffer of 5 mM Tris pH 7.5, 0.5 mM EDTA and 1M NaCl.

To the IMX reagent, stock solutions of the nucleotide compositions were added to yield the final concentrations of 2 µM rbATP-LN3-SS-NR550C4, 10 µM rbCTP-(LN3)$^2$-Biotin, 1 µM rbTTP-LN3-NR550C4 and 2 µM rbGTP-dark. Additionally, 15 µg/ml of a High Density polymerase was added to the IMX/nucleotide reagent. CLM, SMX and PR2 reagents were as previously described. A master mix, SA-NR550C4-Cleavage Mix, was prepared by diluting SA-NR550C4 to a final concentration of 5 µg/ml in 2 mM THP, 5 mM Tris pH 7.4, 1M NaCl, 0.5 mM EDTA and 0.005% Tween.

The one dye sequencing experiments were run on a MiSeq™ sequencing instrument (Illumina, Inc.). The position of the reagents on the instrument was:

1-IMX

2-SRE (Scan Mix)

3-PR2

4-CLM

18-SA-NR550C4-Cleavage Mix

The instrument was set at 60° C. at the beginning of the sequencing experiments and all of the sequencing steps including imaging steps were carried out at this temperature for isothermal sequencing. The isothermal sequencing performed comparably to sequencing performed on the GAIIx as previously described, where imaging took place at 22° C.

For MiSeq™ sequencing, total SBS chemistry cycle time for one incorporation cycle (excluding imaging cycles) was 3.37 minutes (1 dye SBS was 2.70 minutes and SA labelling and cleavage was 0.67 seconds). The sequencing cycles were repeated basically as described in FIG. 12.

Results from the one dye sequencing experiment can be found in FIGS. 5A&D and Table 2. Phasing was reported at 0.17% and prephasing at 0.36%. Table 2 shows results from lane 1, tiles 1-4.

TABLE 2

| Lane | Tile | Clusters (raw) | % PF Clusters | % Align (PF) | Av Alignment Score (PF) | % Error Rate (PF) |
|---|---|---|---|---|---|---|
| 1 | 1 | 331576 | 71.85 | 90.85 | 673.37 | 2.13 |
| 1 | 2 | 331383 | 71.51 | 91.11 | 677.41 | 2.09 |
| 1 | 3 | 334956 | 72.19 | 90.87 | 676.4 | 2.07 |
| 1 | 4 | 333278 | 72.74 | 90.97 | 671.76 | 2.18 |

FIG. 5A shows an example of tracking of error rate percentages of basecalls over a 150 cycle sequencing run for a tile. An error rate of approximately 2.12% over 150 cycles was seen. Based on the experimental design, FIGS. 5B and C show exemplary imaging events of detection patterns that should result for the different modified nucleotides for each of the imaging events. For example, FIG. 5B Image 1 shows that the first image event should capture no, or minimal, fluorescence for rbGTP or rbCTP-(LN3)$^2$-Biotin as they are not associated with any fluorescent moiety prior to the first imaging event and fluorescence for the rbATP and rbTTP labeled nucleotides as they are associated with a fluorescent moiety prior to the first imaging event. FIG. 6C Image 2 shows that following the addition of the SA-NR550C4-Cleavage Mix there should be no, or minimal, fluorescence from the rbATP modified nucleotide as the disulfide in the rbATP-LN3-SS-NR550C4 composition should be cleaved thereby releasing the attached fluorophore and the incorporation of the rbCTP into the growing nucleic acid strand would be detectable due to the binding of the SA-NR550C4 composition to the biotin on the rbCTP-(LN3)$^2$-Biotin conjugate. The rbGTP and rbTTP-LN3-NR550C4 fluorescent patterns should remain the same from Image 1 to Image2 when following the experimental design described in this Example.

FIG. 5D shows a cloud plot demonstrating that, surprisingly, the fluorescence detection pattern did follow the proposed image pattern and that each of the nucleotides could be differentiated one from the other when incorporated into a growing nucleotide strand using only one dye and two imaging events in a sequencing experiment.

These results reported in this disclosure demonstrate that sequencing of a nucleic acid can be accomplished by using as few as one fluorescent dye and less than four imaging events to differentiate the incorporation of all four different nucleic acids in a sequencing cycle.

All publications and patents mentioned in the present application are herein incorporated by reference. Various modifications and variations of the described methods and compositions will be apparent to those skilled in the art without departing from the scope and spirit of the disclosure. Although the invention has been described in connection with specific preferred embodiments, it should be understood that the invention as claimed should not be unduly limited to such specific embodiments. Indeed, various modifications of the described embodiments that are obvious to those skilled in the relevant fields are intended to be within the scope of the following claims.

The invention claimed is:

1. A kit for nucleic acid sequencing, comprising:
a first type of reversibly blocked nucleotide having the structure:

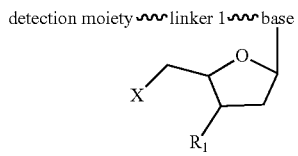

wherein the detection moiety comprises a hapten;
linker 1 comprises a spacer linker, a cleavable linker, or a combination thereof;
the base is a nucleobase;
X is a triphosphate; and
$R_1$ is a blocked 3'-OH group which can be transformed into —OH;
a hapten binding partner labeled with one or more first fluorophores;
a second type of reversibly blocked nucleotide labeled with a second fluorophore via linker 2;
a third type of reversibly blocked nucleotide labeled with a third fluorophore;
a fourth type of reversibly blocked unlabeled nucleotide; and
a chemical reagent that is capable of selectively cleaving the linker 2 but not the linker 1.

2. The kit of claim 1, wherein each of the first fluorophore, the second fluorophore and the third fluorophore are excitable by a single light source.

3. The kit of claim 1, wherein the hapten binding partner comprises streptavidin, and the hapten in the first type of reversibly blocked nucleotide comprises a biotin.

4. The kit of claim 1, further comprising a reducing agent for cleaving the linker 1 of the first type of reversibly blocked nucleotide.

5. The kit of claim 4, wherein the reducing agent is selected from the group consisting of a phosphine compound, a water soluble phosphine, a nitrogen containing phosphine and salts and derivatives thereof, dithioerythritol (DTE), dithiothreitol (DTT), 2-mercaptoethanol, β-mercaptoethanol (BME), aminoethanethiol, glutathione, thioglycolate, thioglycolic acid, 2,3-dimercaptopropanol, tris (2-carboxyethyl)phosphine (TCEP), tris(hydroxymethyl) phosphine (THP), and β-[tris(hydroxymethyl)phosphine] propionic acid (THPP).

6. The kit of claim 1, wherein $R_1$ comprises an azido or an alkoxy group.

7. The kit of claim 6, wherein $R_1$ is —OCH$_2$N$_3$.

8. The kit of claim 1, wherein the hapten in the first type of reversibly blocked nucleotide comprises digoxigenin (DIG), and the hapten binding partner comprises anti-DIG.

9. The kit of claim 1, wherein the hapten in the first type of reversibly blocked nucleotide comprises dinitrophenol (DNP), and the hapten binding partner comprises anti-DNP.

10. The kit of claim 1, wherein the nucleobase in the first type of reversibly blocked nucleotide is selected from the group consisting of A, T and C.

11. The kit of claim 1, wherein each of the linker 1 and the linker 2 independently comprises one or more cleavable moiety selected from the group consisting of a disulfide, a diol, a diazo, an ester, a sulfone, an azido, an allyl, and a silyl ether.

12. The kit of claim 11, wherein the linker 1 comprises an azido moiety.

13. The kit of claim 12, wherein the linker 1 comprises a polyethylene glycol linker and 2-{2-[3-(2-amino-ethylcarbonyl)-phenoxyl-1-azido-ethoxy}-ethoxy-acetic acid derived linker having the structure:

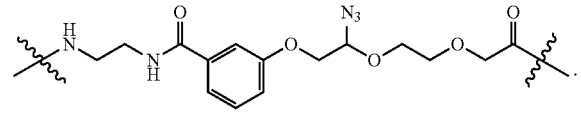 [SMILES: *NCCNC(=O)c1cccc(OCC(N=[N+]=[N-])OCCOCC(*)=O)c1]

14. The kit of claim 1, wherein the first type of reversibly blocked nucleotide has the structure:

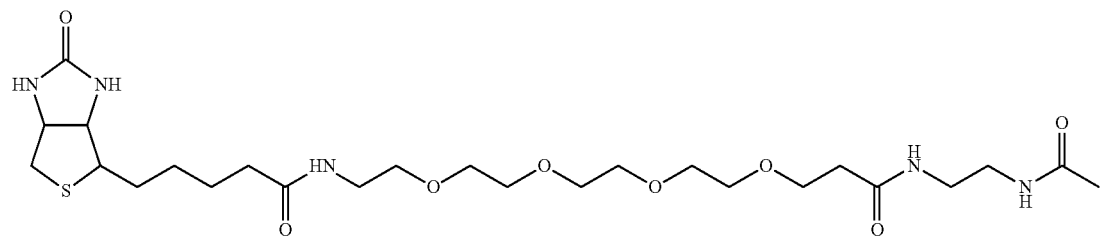

-continued
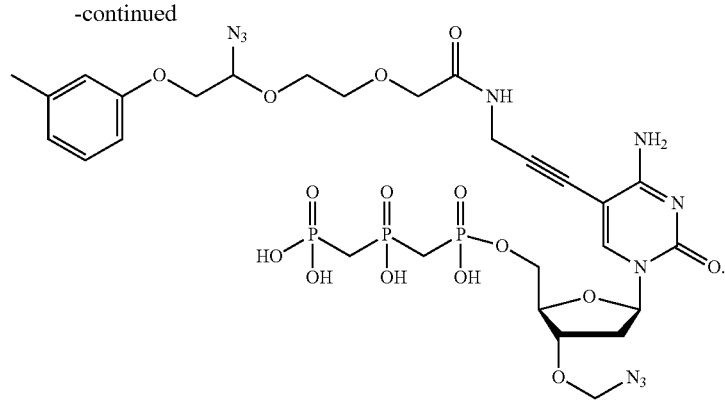
15. The kit of claim 11, wherein the linker 2 comprises a disulfide moiety.
16. The kit of claim 10, wherein the linker 2 comprises a disulfide moiety and an azido moiety.
* * * * *

UNITED STATES PATENT AND TRADEMARK OFFICE
CERTIFICATE OF CORRECTION

| | | |
|---|---|---|
| PATENT NO. | : 11,827,932 B2 | Page 1 of 4 |
| APPLICATION NO. | : 17/153309 | |
| DATED | : November 28, 2023 | |
| INVENTOR(S) | : Robert C. Kain et al. | |

It is certified that error appears in the above-identified patent and that said Letters Patent is hereby corrected as shown below:

In the Specification

Column 23, Line 5 (approx.), delete "S07181" and insert -- SO7181 --.

Column 25, Lines 38-39, delete "carboxynapthofluorescein" and insert
-- carboxynaphthofluorescein --.

Column 26, Line 1, delete "Malacite" and insert -- Malachite --.

Columns 35-36, Lines 50-65 (approx.), delete:

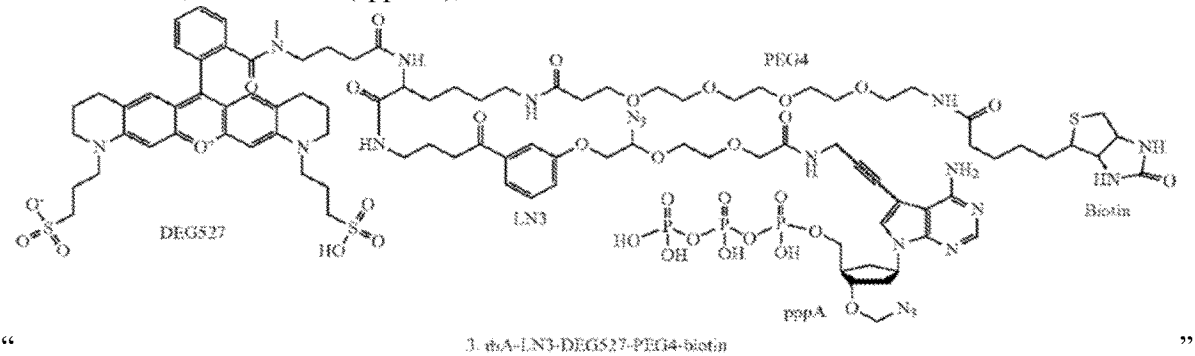

Signed and Sealed this
Twenty-third Day of April, 2024

Katherine Kelly Vidal
*Director of the United States Patent and Trademark Office*

CERTIFICATE OF CORRECTION (continued)
U.S. Pat. No. 11,827,932 B2

And insert:

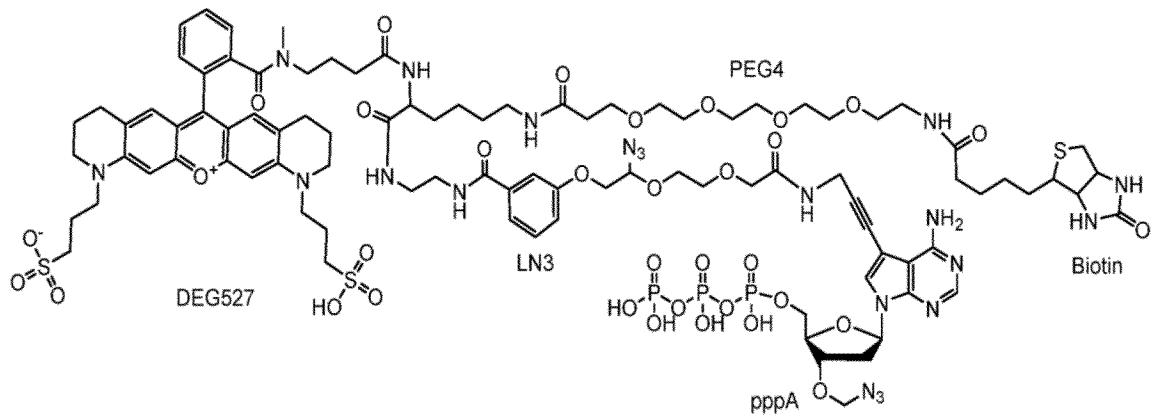

-- 3. rbA-LN3-DEG527-PEG4-biotin --.

Columns 37-38, Lines 30-65 (approx.), delete:

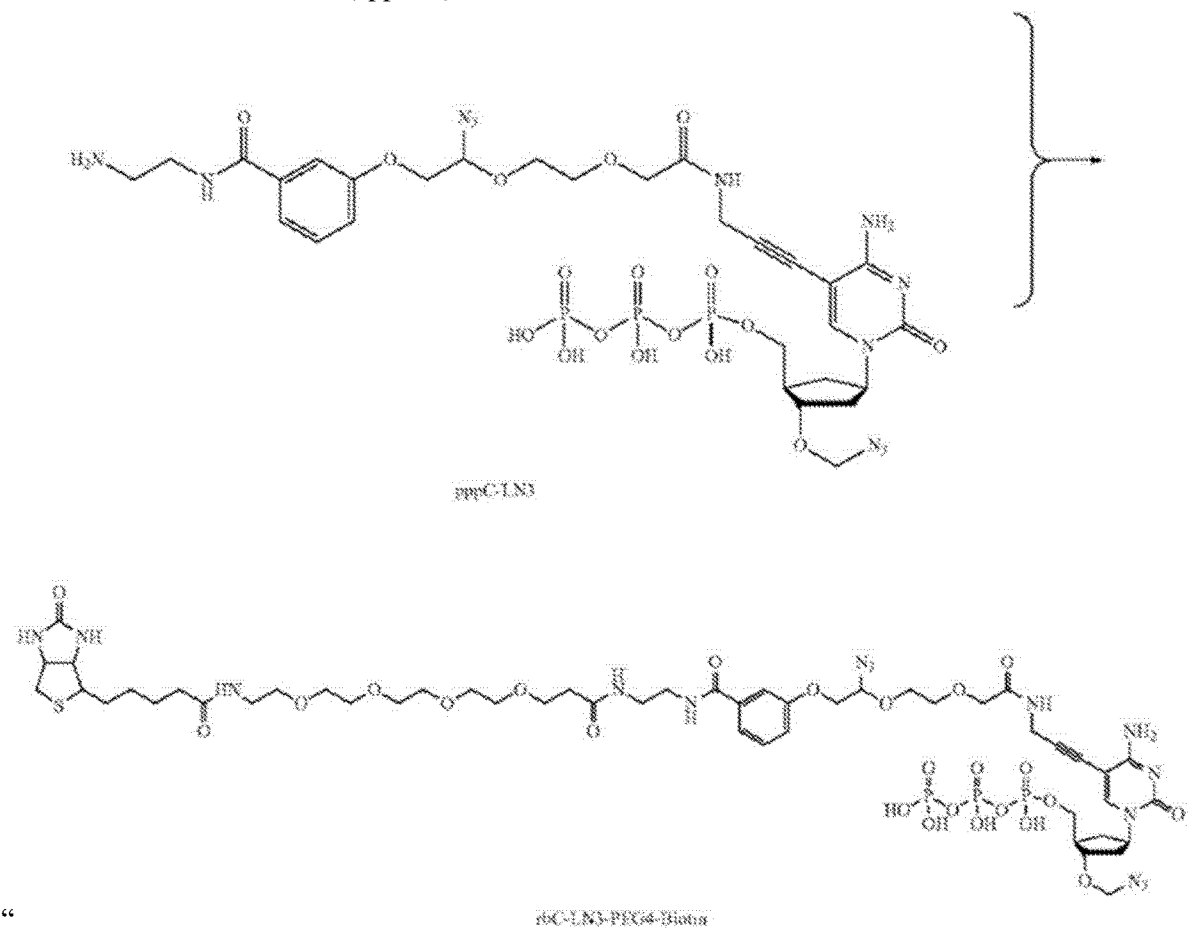

" rbC-LN3-PEG4-Biotin "

CERTIFICATE OF CORRECTION (continued)
U.S. Pat. No. 11,827,932 B2

And insert:

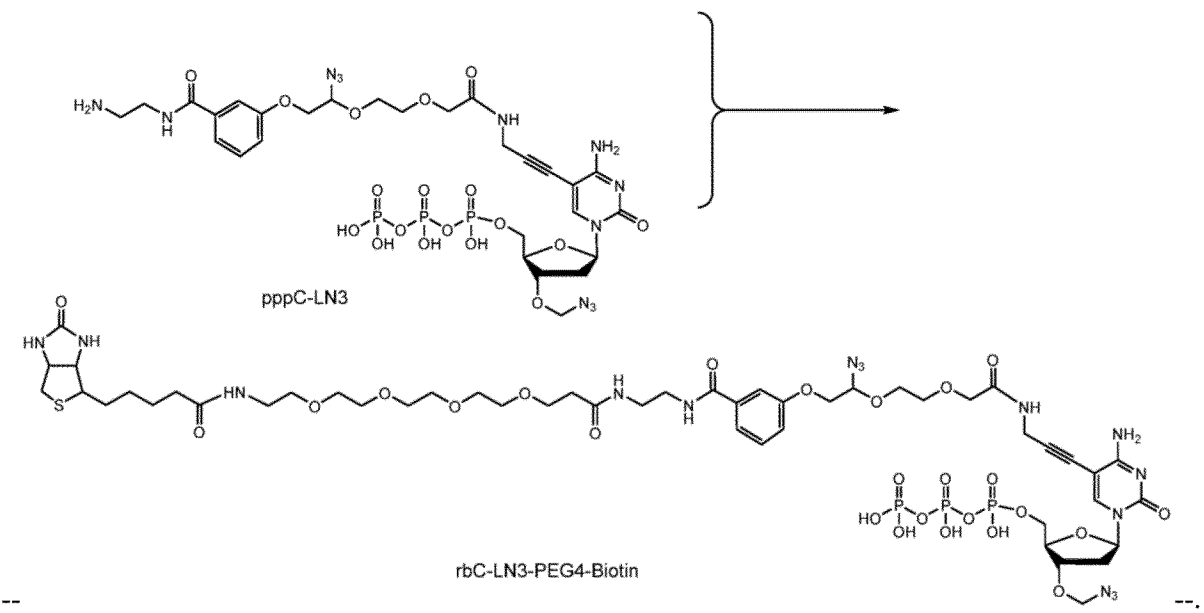

Columns 39-40, Lines 45-55 (approx.), delete:

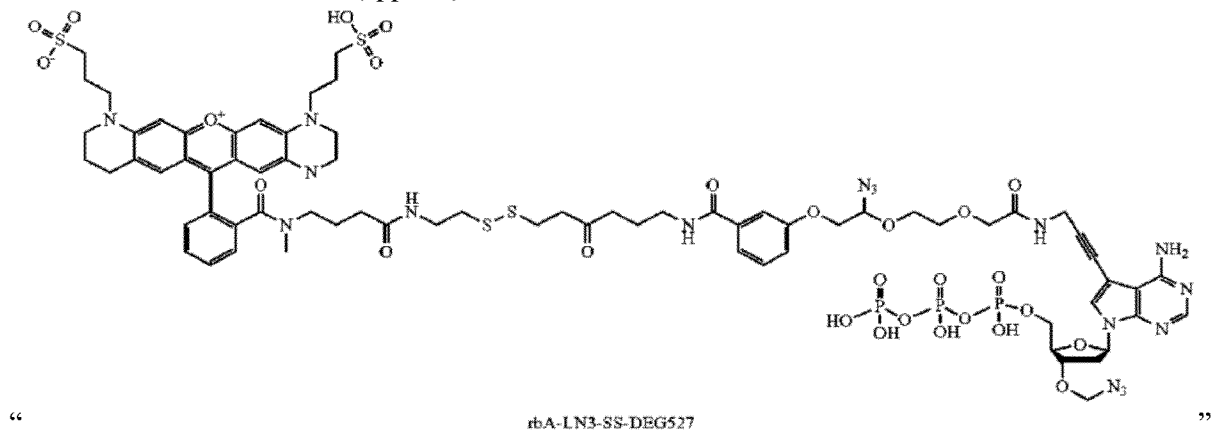

And insert:

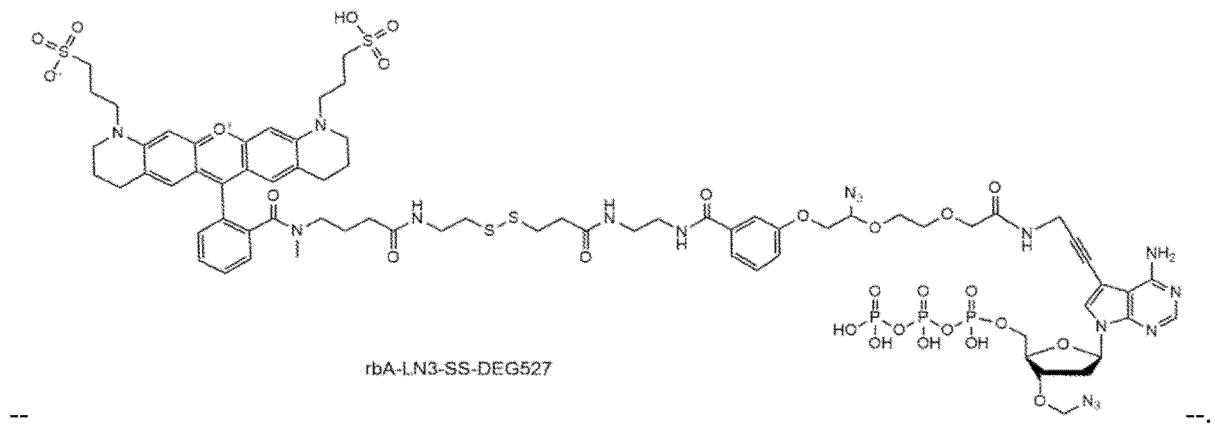

CERTIFICATE OF CORRECTION (continued)
U.S. Pat. No. 11,827,932 B2

In the Claims

Columns 45-46, Lines 55-65 to Columns 47-78, Lines 1-15 (approx.), Claim 14, delete:

"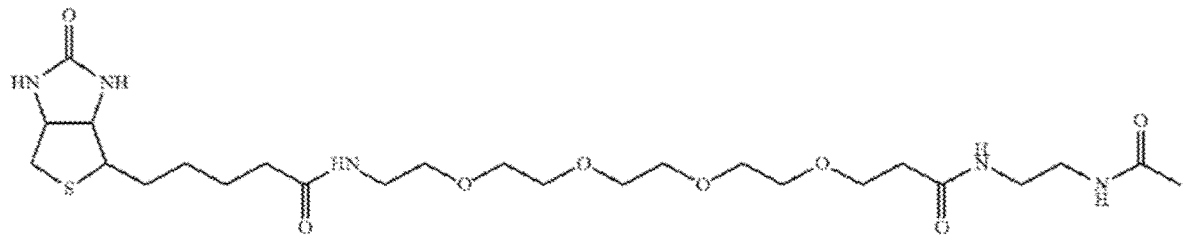

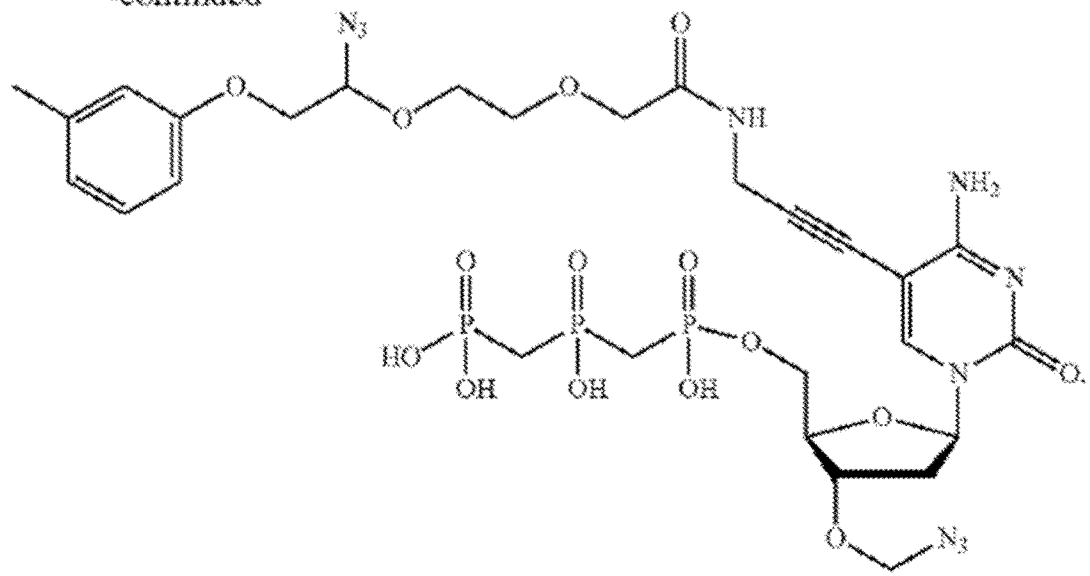
"

And insert:

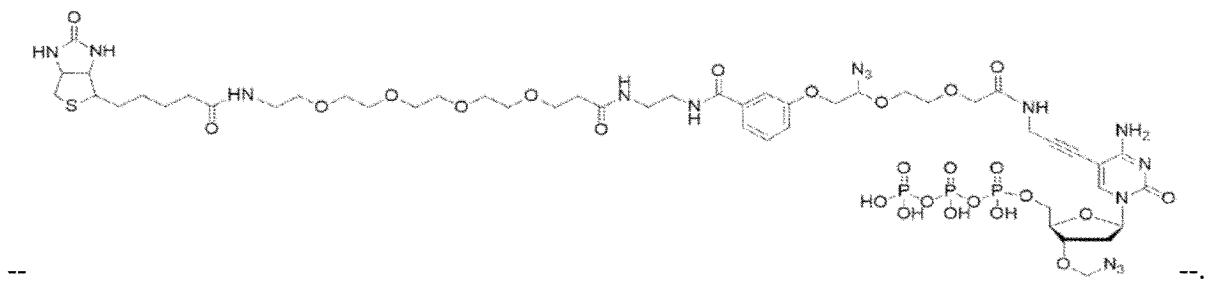

--    --.